United States Patent

Schrock et al.

[11] 3,974,288
[45] Aug. 10, 1976

[54] PENICILLINS

[75] Inventors: Wilfried Schrock; Karl-Georg Metzger; Hans-Bodo Konig, all of Wuppertal, Germany

[73] Assignee: Bayer Aktiengesellschaft, Germany

[22] Filed: Jan. 28, 1975

[21] Appl. No.: 544,812

Related U.S. Application Data

[62] Division of Ser. No. 461,227, April 15, 1974.

[30] Foreign Application Priority Data

Apr. 19, 1974 Germany............................ 2320039

[52] U.S. Cl. ................................................ 424/271
[51] Int. Cl.² ............................................ A61K 31/43
[58] Field of Search .................................... 424/271

[56] References Cited
UNITED STATES PATENTS 3,433,784  3/1969  Long et al...................... 260/239.1
3,518,253  6/1970  Foskev et al.................. 260/239.1

FOREIGN PATENTS OR APPLICATIONS 1,061,335  5/1967  United Kingdom............. 260/239.1

Primary Examiner—Jerome D. Goldberg

[57] ABSTRACT

A compound of the formula:

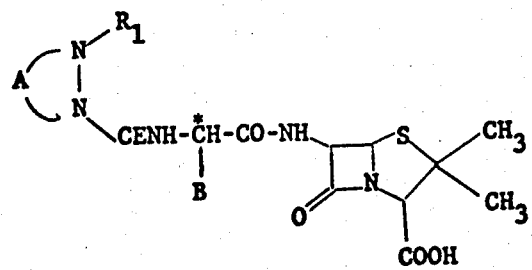

or a pharmaceutically acceptable nontoxic salt thereof wherein
$R_1$ is hydrogen, straight or branched chain alkyl of 1 to 5 carbon atoms, monoaralkyl of up to 8 carbon atoms, monoaryl, substituted monoaryl, or thienyl;
A is moiety of the formula:

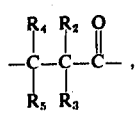

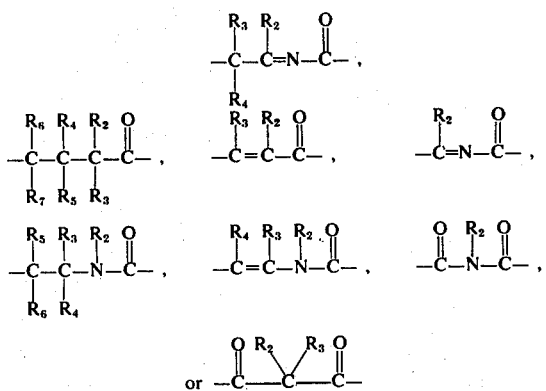

wherein
$R_2$, $R_3$, $R_4$, $R_5$, $R_6$ and $R_7$ are the same or different and each is hydrogen, straight or branched chain alkyl of 1 to 5 carbon atoms, monoaralkyl of up to 8 carbon atoms, monoaryl, substituted monoaryl, or thienyl;
B is a moiety of the formula:

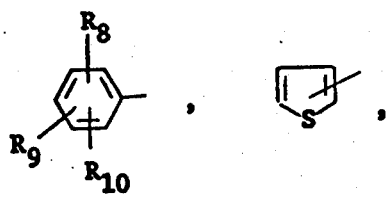

wherein
$R_8$, $R_9$ and $R_{10}$ are the same or different and each is hydrogen, fluorine, chlorine, bromine. iodine, lower alkyl, lower alkoxy, lower alkylthio, lower alkylsulphonyl, sulphamyl, nitro, cyano, di(lower alkyl)amino, lower alkanoylamino, lower alkanoyloxy, lower alkylsulphonylamino, trifluoromethyl or hydroxy;
E is oxygen or sulphur; and
C is a carbon atom constituting a center of chirality, are useful for their antibacterial activity.

127 Claims, No Drawings

PENICILLINS

This is a division of application Ser. No. 461,227 filed Apr. 15, 1974.

The present invention relates to penicillins, to a process for their production, to pharmaceutical compositions useful for their antibacterial activity wherein said penicillins are the active agents, to methods of treating bacterial infections in humans and animals using said penicillins, to animal feedstuff compositions embodying said penicillins and to the use of said penicillins as growth promoting agents for use with animals.

It is known that acetamidopenicillanic acids which in the α-position of the acetamido moiety carry an aryl group and an acyl semicarbazide moiety are synthetically obtainable and exhibit antibacterial activity. See British Pat. No. 1,061,335. However according to that patent, none of the penicillins disclosed have a hydrazine group of the acyl semicarbazide formed into a heterocyclic ring.

More particularly, the present invention is concerned with penicillins of the formula:

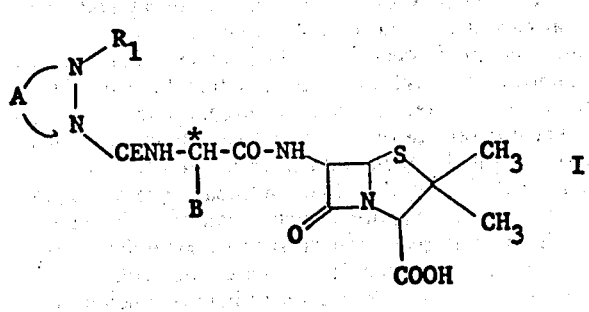

and pharmaceutically acceptable nontoxic salts thereof wherein
$R_1$ is hydrogen, straight or branched chain alkyl of 1 to 5 carbon atoms, aralkyl of up to 8 carbon atoms, aryl preferably monoaryl, substituted aryl preferably substituted monoaryl, or thienyl;
A is a moiety of the formula:

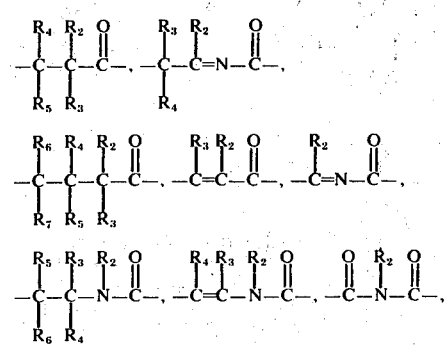

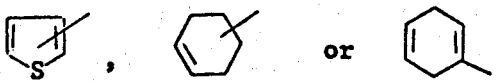

wherein
$R_2$, $R_3$, $R_4$, $R_5$, $R_6$ and $R_7$ are the same or different and each is hydrogen, straight or branched chain alkyl of 1 to 5 carbon atoms, aralkyl of up to 8 carbon atoms, aryl preferably monoaryl, substituted aryl preferably substituted monoaryl, or thienyl;
B is a moiety of the formula:

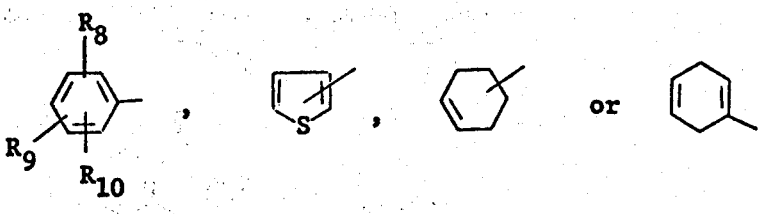

wherein
$R_8$, $R_9$ and $R_{10}$ are the same or different and each is hydrogen, fluorine, chlorine, bromine, iodine, lower alkyl, lower alkoxy, lower alkylthio, lower alkylsulphonyl, sulphamyl, nitro, cyano, di(lower alkyl)amino, lower alkanoylamino, lower alkanoyloxy, lower alkylsulphonylamino, trifluoromethyl or hydroxy;
E is oxygen or sulphur; and
*C is a carbon atom constituting a center of chirality which may be either racemic or either of the R- or S- configurations.

These penicillins are particularly useful for their antibacterial activity.

As used herein, the phrase "compounds of the present invention" include both the penicillins in the form of the free acid and in the form of pharmaceutically acceptable nontoxic salts.

The preferred salts of the penicillins of the present invention include the sodium, potassium, magnesium, calcium, aluminum and ammonium salts, as well as di- and tri-lower alkylamines, procaine, dibenzylamine, N,N'-dibenzylethylenediamine, N-benzyl-β-phenethylamine, N-methylmorpholine and N-ethylmorpholine, 1-ephenamine, dehydroabietylamine, N,N'-bis-dehydroabietylethylenediamine, N-lower alkylpiperidine, as well as other amines which are known to form salts of penicillins.

The phrase "lower alkyl" includes straight as well as branched chain alkyl moieties of 1 to 6 carbon atoms.

The penicillins of the present invention may be produced by reacting a compound of the formula:

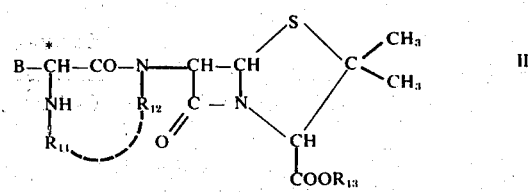

wherein
B and C* are as defined above; and
either
(a) $R_{11}$, $R_{12}$ and $R_{13}$ are each hydrogen;
or
(b) $R_{11}$ ... $R_{12}$ is the moiety —$C(R_{14})_2$— and $R_{13}$ is hydrogen;
or
(c) $R_{11}$ and $R_{12}$ are each hydrogen and $R_{13}$ is a trialkylsilyl, preferably tri-loweralkylsilyl of the formula:

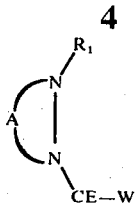

wherein
$R_1$, A and E are as above defined; and
W is halogen, azido or

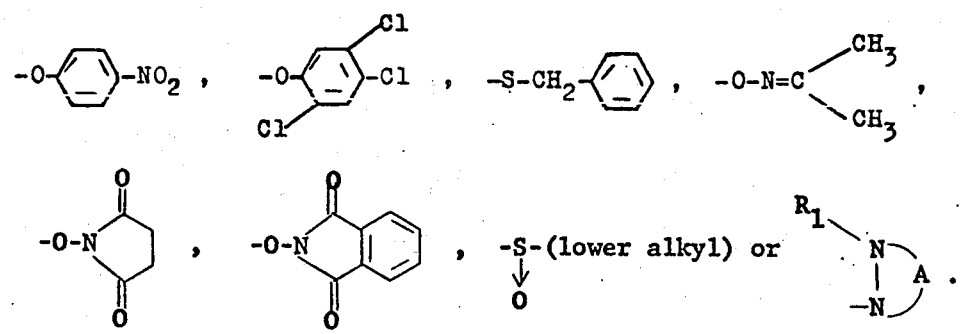

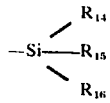

wherein $R_{14}$, $R_{15}$ and $R_{16}$ are each lower alkyl;
or
(d) $R_{11}$ and $R_{13}$ are trialkylsilyl, preferably tri-loweralkylsilyl of the formula:

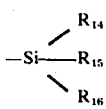

wherein $R_{14}$, $R_{15}$ and $R_{16}$ are as above defined; and $R_{12}$ is hydrogen;
with a compound of the formula:

When $R_{11}$ or $R_{12}$ and $R_{13}$ are as defined in (a) or (b), the reaction is carried out in the presence of a base or buffer. When $R_{11}$, $R_{12}$ and $R_{13}$ are as defined in (c) or (d), the reaction is carried out either in the presence or the absence of a base or buffer. The reaction temperature is from −20° to about +50°C.

The penicillins of the present invention and their pharmaceutically acceptable nontoxic salts may be interconverted according to techniques which are per se known, such as for example reacting the penicillin in the form of a free acid with a suitable base.

The compounds of the present invention are particularly useful for their antibacterial activity especially against the family Pseudomonadaceae. The penicillins of the present invention display greater activity against Pseudomonadaceae than do such commercially available penicillins as Ampicillin and Carbenicillin.

If, for example D(-)-α-amino-benzylpenicillin and 1-chlorocarbonyl-3-oxo-pyrazolidine are used as starting substances, the course of the reaction can be illustrated by the following equation:

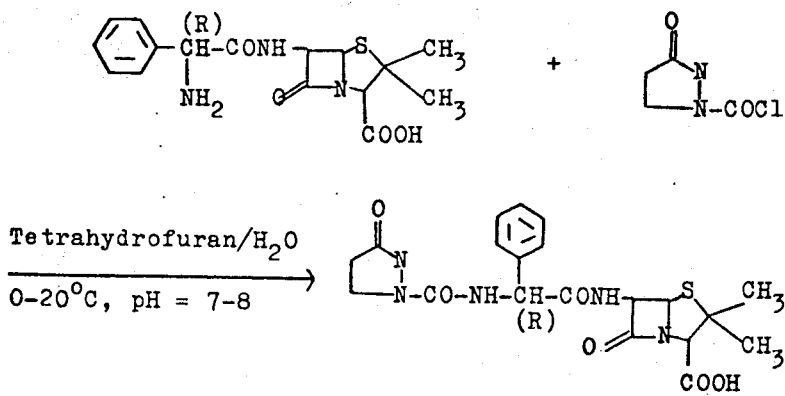

According to one embodiment of the present invention:

$R_1$ is hydrogen, or straight or branched chain alkyl of 1 to 4 carbon atoms;

A is a moiety of the formula:

$$-\underset{R_5}{\overset{R_4}{C}}-\underset{R_3}{\overset{R_2}{C}}-\overset{O}{\underset{}{C}}-,$$

$$-\underset{R_4}{\overset{R_3}{C}}-\overset{R_2}{\underset{}{C}}=N-\overset{O}{\underset{}{C}}-,$$

$$-\underset{R_7}{\overset{R_6}{C}}-\underset{R_5}{\overset{R_1}{C}}-\underset{R_3}{\overset{R_2}{C}}-\overset{O}{\underset{}{C}}-, -\overset{R_3}{\underset{}{C}}=\overset{R_2}{\underset{}{C}}-\overset{O}{\underset{}{C}}- \text{ or } -\overset{O}{\underset{}{C}}-\overset{R_2}{\underset{}{N}}-\overset{O}{\underset{}{C}}-,$$

wherein $R_2, R_3, R_4, R_5, R_6$ and $R_7$ are the same or different and each is hydrogen, alkyl of 1 to 4 carbon atoms, phenyl or hydroxyphenyl;

B is a moiety of the formula:

[chemical structures showing substituted phenyl with $R_8$, $R_9$, $R_{10}$, thienyl, or cyclohexadienyl]

wherein $R_8$, $R_9$ and $R_{10}$ are the same or different and each is hydrogen, fluorine, chlorine, bromine, iodine, lower alkyl, lower alkoxy, lower alkylthio, lower alkylsulphonyl, sulphamyl, nitro, cyano, di(lower alkyl)amino, lower alkanoylamino, lower alkanoyloxy, lower alkylsulphonylamino, trifluoromethyl or hydroxy.

According to another embodiment of the present invention:

$R_1$, A and B are as defined in the immediately preceding embodiment, and

C is in the R- configuration.

According to another embodiment of the present invention:

$R_1$ is hydrogen;

A is a moiety of the formula:

$$-\underset{R_5}{\overset{R_4}{C}}-\underset{R_3}{\overset{R_2}{C}}-\overset{O}{\underset{}{C}}- \text{ or } -\overset{R_3}{\underset{}{C}}=\overset{R_2}{\underset{}{C}}-\overset{O}{\underset{}{C}}-$$

wherein $R_2, R_3, R_4$ and $R_5$ are the same or different and each is hydrogen or methyl;

B is phenyl, hydroxyphenyl, thienyl or cyclohexadien-1-yl.

According to another embodiment of the present invention:

$R_1$, A and B are as defined in the immediately preceding embodiment, and

C is in the R-configuration.

According to another embodiment of the present invention:

$R_1$ is hydrogen or lower alkyl;

A is a moiety of the formula:

$$-\underset{R_5}{\overset{R_4}{C}}-\underset{R_3}{\overset{R_2}{C}}-\overset{O}{\underset{}{C}}-, -\underset{R_4}{\overset{R_3}{C}}-\overset{R_2}{\underset{}{C}}=N-\overset{O}{\underset{}{C}}-,$$

$$-\underset{R_7}{\overset{R_6}{C}}-\underset{R_5}{\overset{R_1}{C}}-\underset{R_3}{\overset{R_2}{C}}-\overset{O}{\underset{}{C}}-, -\overset{R_3}{\underset{}{C}}=\overset{R_2}{\underset{}{C}}-\overset{O}{\underset{}{C}}- \text{ or } -\overset{O}{\underset{}{C}}-\overset{R_2}{\underset{}{N}}-\overset{O}{\underset{}{C}}-$$

wherein $R_2, R_3, R_4, R_5, R_6$ and $R_7$ are each hydrogen, or one is alkyl of 1 to 4 carbon atoms, phenyl or nitrophenyl and the rest are each hydrogen, or two are each methyl and the rest are each hydrogen;

B is phenyl, hydroxyphenyl or cyclohexadien-1-yl;

and

C is in the R- configuration.

According to another embodiment of the present invention:

$R_1$ is hydrogen or methyl;

A is a moiety of the formula:

$$-\underset{R_5}{\overset{R_4}{C}}-\underset{R_3}{\overset{R_2}{C}}-\overset{O}{\underset{}{C}}-, -\underset{R_4}{\overset{R_3}{C}}-\overset{R_2}{\underset{}{C}}=N-\overset{O}{\underset{}{C}}-,$$

$$-\underset{R_7}{\overset{R_6}{C}}-\underset{R_5}{\overset{R_4}{C}}-\underset{R_3}{\overset{R_2}{C}}-\overset{O}{\underset{}{C}}-, -\overset{R_3}{\underset{}{C}}=\overset{R_2}{\underset{}{C}}-\overset{O}{\underset{}{C}}- \text{ or } -\overset{O}{\underset{}{C}}-\overset{R_2}{\underset{}{N}}-\overset{O}{\underset{}{C}}-$$

wherein $R_2, R_3, R_4, R_5, R_6$ and $R_7$ are each hydrogen or one is methyl, ethyl, phenyl or nitrophenyl and each of the rest is hydrogen, or two are each methyl and the rest are each hydrogen;

B is phenyl, p-hydroxyphenyl or cyclohexadien-1-yl;

and

C is in the R- configuration.

According to another embodiment of the present invention:

$R_1$ is hydrogen, or alkyl of 1 or 2 carbon atoms;

A is a moiety of the formula:

$$-\underset{R_5}{\overset{R_4}{C}}-\underset{R_3}{\overset{R_2}{C}}-\overset{O}{\underset{}{C}}-, -\underset{R_4}{\overset{R_3}{C}}-\overset{R_2}{\underset{}{C}}=N-\overset{O}{\underset{}{C}}-,$$

$$-\underset{R_7}{\overset{R_6}{C}}-\underset{R_5}{\overset{R_4}{C}}-\underset{R_3}{\overset{R_2}{C}}-\overset{O}{\underset{}{C}}-, -\overset{R_3}{\underset{}{C}}=\overset{R_2}{\underset{}{C}}-\overset{O}{\underset{}{C}}- \text{ or } -\overset{O}{\underset{}{C}}-\overset{R_2}{\underset{}{N}}-\overset{O}{\underset{}{C}}-$$

wherein $R_2, R_3, R_4, R_5, R_6$ and $R_7$ are each hydrogen or one is alkyl of 1 to 4 carbon atoms, phenyl or nitrophenyl and each of the rest is hydrogen, or two are each methyl and each of the rest is hydrogen;

B is phenyl; phenyl substituted by fluorine, chlorine, bromine, lower alkyl, lower alkoxy, nitro, cyano, di(lower alkyl)amino, lower alkanoylamino, lower alkanoyloxy, sulphamyl, hydroxy or dihydroxy; *cyclohexadien-1-yl; or thienyl; and C is in the R- configuration.

According to another embodiment of the present invention:

$R_1$ is hydrogen or methyl;

A is a moiety of the formula:

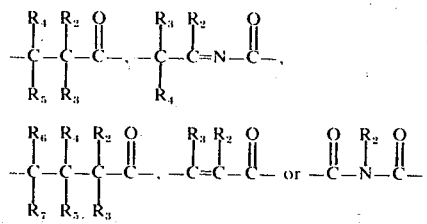

wherein $R_2$, $R_3$, $R_4$, $R_5$, $R_6$ and $R_7$ are each hydrogen or one is methyl, ethyl, phenyl or nitrophenyl and each of the reset is hydrogen, or two are each methyl and the rest are each hydrogen;

B is phenyl; phenyl substituted by hydroxy, methyl, fluoro, chloro, nitro, cyano, methoxy, acetoxy, acetamido, dimethylamino, sulphamyl, or dihydroxy; cyclohexadien-1-yl; or thienyl; and
*C is in the R- configuration.

According to another embodiment of the present invention, the salt of the compound of formula I is selected from the group consisting of sodium, potassium, magnesium, calcium, aluminum, ammonium, a di(lower alkyl)amine, a tri(lower alkyl)amine, procaine, dibenzylamine, N,N'-dibenzylethylenediamine, N-benzyl-β-phenethylamine, N-methylmorpholine, N-ethylmorpholine, 1-ephenamine, dehydroabietylamine, N,N'-bis-dehydroabietylethylenediamine, or N-lower alkylpiperidine.

According to another embodiment of the present invention, a compound of formula I is in the form of the sodium salt wherein *C is in the R- configuration.

According to another embodiment of the present invention:

$R_{11}$, $R_{12}$ and $R_{13}$ are each hydrogen, or $R_{12}$ is hydrogen and $R_{11}$ and $R_{13}$ are $-Si(CH_3)_3$; and W is chlorine.

Representative compounds of formula II above which are used as starting materials in the process according to the present invention are known. Their preparation is described in German Pat. No. 1,156,078, South Africa Pat. No. 68/8,290, Netherlands Pat. No. 68/18,057, Belgian Pat. No. 737,451, U.S. Pat. Nos. 2,985,648, 3,140,282, 3,144,445, 3,157,640 and 3,342,677 and J. Chem. Soc. (C), 1971, 1920 and J. Med. Chem. 14, 117 (1971).

Compounds of the formula II which are not previously known and in which $R_{11}$, $R_{12}$ and $R_{13}$ are hydrogen can be prepared, for example, from 6-aminopenicillanic acid entirely analogously to the method described in German Pat. No. 1,156,078.

Those compounds of the formula II wherein $R_{11}$ ... $R_{12}$ is $-C(R_{14})_2-$ and $R_{13}$ is hydrogen that are used as starting materials in the process according to the present invention, and which are not previously known, can be prepared by condensation of compounds of the formula II wherein $R_{11}$, $R_{12}$ and $R_{13}$ are hydrogen, with carbonyl compounds $R_{14}-CO-R_{14}$, wherein $R_{14}$ is as defined above, with elimination of water.

Those compounds of the formula II used as starting materials wherein $R_{12}$ is hydrogen and $R_{11}$ and $R_{13}$ are trialkylsilyl or wherein $R_{11}$ and $R_{12}$ are hydrogen and $R_{13}$ is a trialkylsilyl can, where they are not previously known, be prepared by reaction of a compound of the formula II, wherein $R_{11}$, $R_{12}$ and $R_{13}$ are hydrogen, with silylating agents, such as trimethylchlorosilane or hexamethyldisilazane, in the presence of acid-binding agents such as triethylamine.

The compounds of the present invention include the racemates, optical isomers and epimers, and all crystalline forms including the anhydrous and hydrated forms such as the mono-, di- and trihydrates.

The configuration of the asymmetric centers of the 6-aminopenicillanic acid nucleus in the compounds of the formula II should be identical with that of the corresponding asymmetric centers of 6-aminopenicillanic acid which has been obtained, for example, from penicillin G by fermentative processes.

Those compounds of the formula III, used as starting materials in the process of the present invention, that have not previously been disclosed can be prepared from the corresponding heterocyclic hydrazine compound of the formula IV, such as for example pyrazolidine, and the appropriate compound of the formula W—CE—W, such as for example phosgene, in an inert organic solvent, such as for example tetrahydrofurane, or in a mixture of warter and an inert organic solvent, such as for example chloroform, in the presence of a base, such as for example triethylamine.

IV wherein $R_1$ and A are as above defined.

Illustrations of their synthesis are provided in more detail in the following examples. However, when W is not halogen, the desired compounds of formula III can also be prepared from a compound of the formula III wherein W is halogen by reaction with a compound of the formula H-W wherein W is as defined above but is not halogen, in the presence of a base such as triethylamine, and in an inert organic solvent, such as tetrahydrofuran, or a mixture of water and an inert organic solvent, such as chloroform.

Diluents which can be used are the substances mentioned in the paragraphs which follow.

If the starting materials used for the synthesis of the compounds of the invention are compounds of formula II in which either (a) $R_{11}$, $R_{12}$ and $R_{13}$ are hydrogen or (b) $R_{11}$ ... $R_{12}$ is $-C(R_{14})_2-$ and $R_{13}$ is hydrogen, the reaction in the process of the invention can be carried out in, for example, a mixture of water with a water-miscible organic solvent, such as acetone, tetrahydrofuran, dioxane, acetonitrile, dimethylformamide, dimethylsulphoxide or isopropanol. The pH of the reaction mixture is kept, for example, between 6.5 and 8.0 by addition of bases or use of buffer solutions. The same reaction can however also be carried out in other pH ranges, for example, at 4.5 to 9.0, or at pH 2.0 to 4.5. It is also possible to carry out the reaction in a water-immiscible solvent, for example chloroform or methylene chloride, with the addition of, preferably, triethylamine, diethylamine, or N-ethylpiperidine as a base. The reaction can also be carried out in a mixture of water and a water-immiscible solvent, such as ether, chloroform, methylene chloride, carbon disulphide, isobutyl methyl ketone, ethyl acetate or benzene, the mixture preferably being vigorously stirred and the pH maintained at the desired value (e.g. between 4.5 and 9.0 or 2.0 and 3.0) by the addition of a base or the use of a buffer solution. The reaction can however also be carried out in water as the sole vehicle in the absence of any organic solvent and in the presence of an organic or inorganic base or a buffer.

When a compound of the formula II is used in which two of the radicals $R_{11}$, $R_{12}$ and $R_{13}$ are trialkylsilyl and the other is a hydrogen radical, the reaction must in most cases be carried out in a solvent which is anhydrous and free of hydroxyl groups, for example, methylene chloride, chloroform, benzene, tetrahydrofurane, acetone or dimethylformamide. The addition of bases is not necessary in such a case but does enable the yield and purity of the product to be improved in some cases. Admittedly, the converse effect is also possible. The optionally added base must either be a tertiary amine, such as pyridine or triethylamine, or a secondary amine which are difficult to acylate as a result of steric hindrance, such as dicyclohexylamine. The number of bases that can be used is therefore very large.

The amount of base used is decided, for example, by the desired adherence to a certain pH. Where a pH measurement and adjustment is not carried out or, because of the absence of sufficient amounts of water in the diluent, it is not possible or not meaningful, 2 mol equivalents of base are preferably used where a compound of the formula II is used in which $R_{11}$, $R_{12}$ and $R_{13}$ are all hydrogen, or $R_{11}$ and $R_{12}$ together are $-C(R_{14})_2-$ and $R_{13}$ is hydrogen, while either no base at all or, preferably, 1 mol equivalent of base is added when two of $R_{11}$, $R_{12}$ and $R_{13}$ are trialkylsilyl and the other is hydrogen.

The reaction temperatures can be varied over a substantial range. The reaction is preferably carried out between 0° and +20°C. As with most chemical reactions, higher or lower temperatures than those indicated in the examples can be used. However, if the values indicated there are exceeded substantially, side-reactions will increasingly occur, which reduce the yield or have an adverse influence on the purity of the products. On the other hand, excessively lowered reaction temperatures reduce the reaction rate so greatly that the yield may become reduced.

The reaction can be carried out under atmospheric pressure but also under reduced or elevated pressure. In general, atmospheric pressure is used.

In carrying out the process according to the invention, the reactants can be reacted with one another in equimolecular amounts. However, it can be desirable to use one of the two reactants in excess in order to facilitate the purification, or preparation in pure form, of the desired compound of the invention and to increase the yield.

For example, the reactants of the formula II can be employed in an excess of 0.1 to 0.3 mol equivalents, and less decomposition of the reactants of the formula III in an aqueous solvent mixture can be achieved thereby. The excess of the reactants of the formula II can easily be removed during working up of the reaction mixture, owing to their good solubility in aqueous mineral acids.

However, it is also possible with advantage to employ the reactants of the formula III in an excess of, for example, 0.1 to 1.0 mol equivalent. This results in better utilization of the reactants of the formula II, and the decomposition of the reactants of the formula III, which occurs as a side-reaction in aqueous solvents, is compensated for. Since the compounds of the formula III added in excess rapidly become converted, in water, into neutral nitrogen-containing heterocyclic compounds which can easily be removed, the purity of the compounds of the invention obtained is hardly impaired thereby.

The reaction mixture resulting from the reaction described above can be worked up in the manner generally known for penicillins.

If the starting material used is a compound of the formula II which contains a moiety $-C(R_{14})_2-$, the hydrolytic splitting off of the fragment $-C(R_{14})_2-$ in the form of the carbonyl compound $R_{14}-CO-R_{14}$ which was originally used to prepare the compound of the formula II, takes place immediately after the reaction of the compound II with the compound of the formula III if water is present in the reaction medium, or during working up of the reaction mixture under aqueous conditions, if no water is present in the reaction medium.

If a compound of the formula II is used in which two of $R_{11}$, $R_{12}$ and $R_{13}$ are trimethylsilyl moieties is used as the starting material, the hydrolytic splitting-off of the trialkylsilyl radicals takes place during working up the reaction mixtures under aqueous conditions.

The following may be mentioned individually as examples of new active compounds of the invention:

D(-)-α-[(4-Methyl-5-oxo-3-pyrazolin-2-yl)-carbonylamino]-benzylpenicillin:

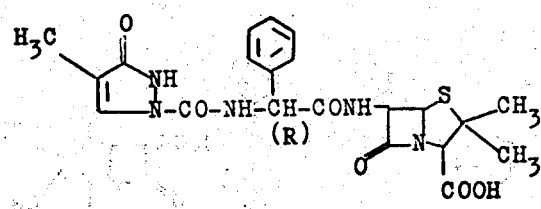

or the sodium salt thereof.
D(-)-α-[(4-Phenyl-5-oxo-3-pyrazolin-2-yl)-carbonylamino]-benzylpenicillin:

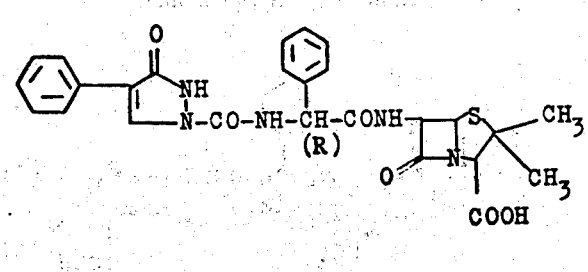

or the sodium salt thereof.
D(-)-α-[(3-Methyl-5-oxo-3-pyrazolin-2-yl)-carbonylamino]-benzylpenicillin:

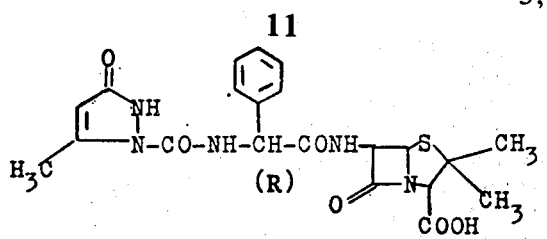

or the sodium salt thereof.
D(-)-α-[(3-Phenyl-5-oxo-3-pyrazolin-2-yl)-carbonylamino]-benzylpenicillin:

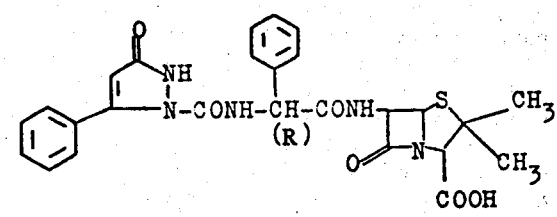

or the sodium salt thereof.
D(-)-α-[(3-p-Nitrophenyl-5-oxo-3-pyrazolin-2-yl)-carbonylamino]-benzylpenicillin:

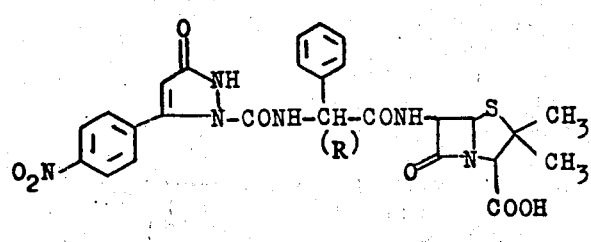

or the sodium salt thereof.
D(-)-α-[(3-m-Nitrophenyl-5-oxo-3-pyrazolin-2-yl)-carbonylamino]-benzylpenicillin:

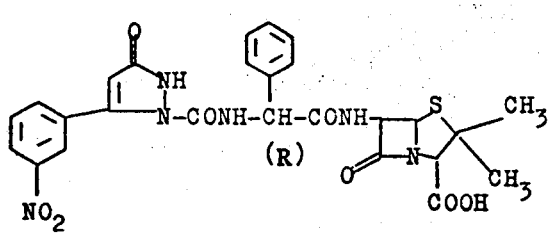

or the sodium salt thereof.
D(-)-α-[(2-Methyl-4-phenyl-5-oxo-3-pyrazolin-1-yl)-carbonylamino]-benzylpenicillin:

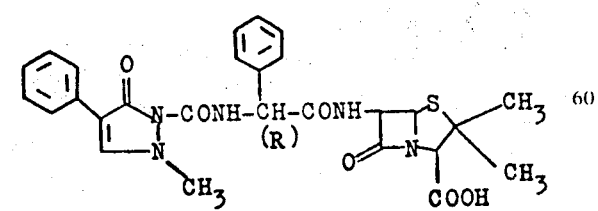

or the sodium salt thereof.
D(-)-α-[(5-Oxo-3-pyrazolin-2-yl)-carbonylamino]-benzylpenicillin:

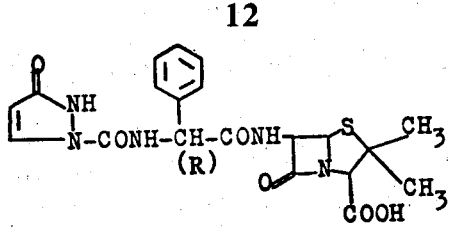

or the sodium salt thereof.
D(-)-α-[(4-Methyl-5-oxo-3-pyrazolin-2-yl)-carbonylamino]-p-hydroxy-benzylpenicillin:

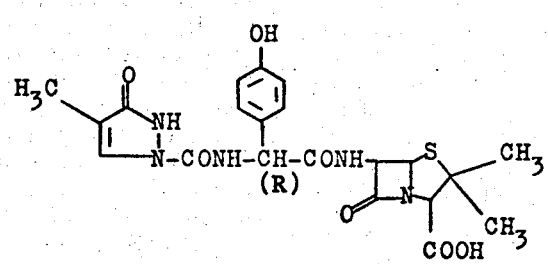

or the sodium salt thereof.
D(-)-α-[(4-Methyl-5-oxo-3-pyrazolin-2-yl)-carbonylamino]-α-(cyclohexa-1,4-dien-1-yl)-methylpenicillin:

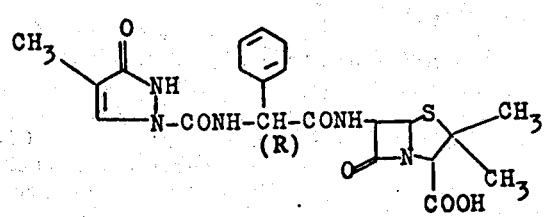

or the sodium salt thereof.
D(-)-α-[(5-Oxo-3-pyrazolin-2-yl)-carbonylamino]-p-hydroxy-benzylpenicillin:

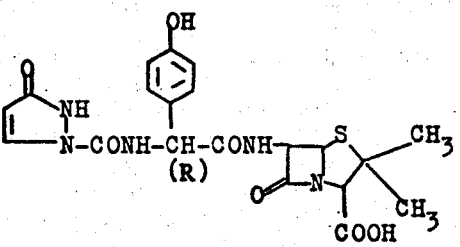

or the sodium salt thereof.
D(-)-α-[(5-Oxo-3-pyrazolin-2-yl)-carbonylamino]-α-(cyclohexa-1,4-dien-1-yl)-methylpenicillin:

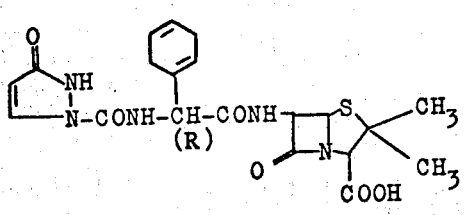

or the sodium salt thereof.
D(-)-α-[(3-Oxo-pyrazolidin-1-yl)-carbonylamino]-benzylpenicillin:

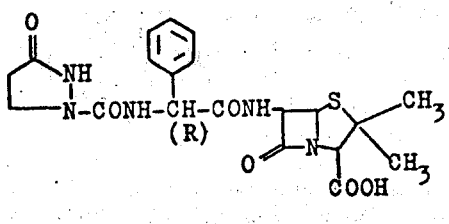

or the sodium salt thereof.
D(-)-α-[(3-Oxo-pyrazolidin-1-yl)-carbonylamino]-α-(cyclohexa-1,4-dien-1-yl)-methylpenicillin:

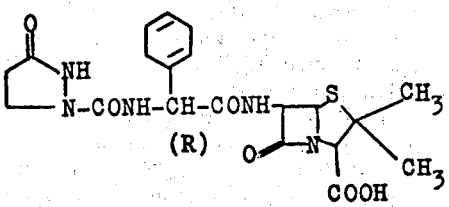

or the sodium salt thereof.
D(-)-α-[(3-Oxo-pyrazolidin-1-yl)-carbonylamino]-p-hydroxy-benzylpenicillin:

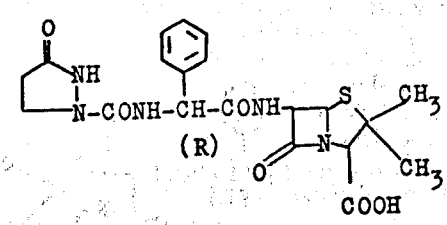

or the sodium salt thereof.
D(-)-α-[(3-Oxo-4-methyl-pyrazolidin-1-yl)-carbonylamino]-benzylpenicillin:

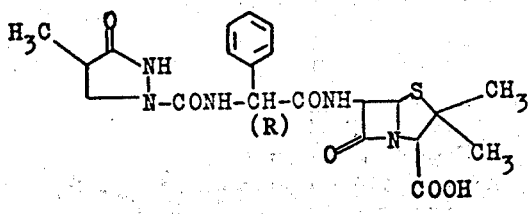

or the sodium salt thereof.
D(-)-α-[(3-Oxo-5-methyl-pyrazolidin-1-yl)-carbonylamino]-benzylpenicillin:

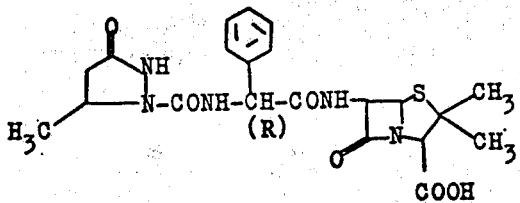

or the sodium salt thereof.

D(-)-α-[(3-Oxo-5,5-dimethyl-pyrazolidin-1-yl)-carbonylamino]-benzylpenicillin:

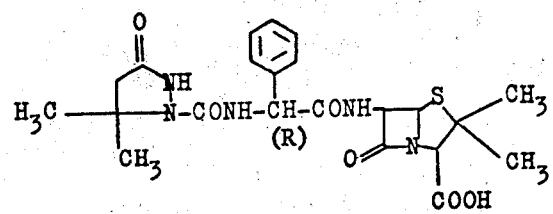

or the sodium salt thereof.
D(-)-α-[(3-Oxo-5-phenyl-pyrazolidin-1-yl)-carbonylamino]-benzylpenicillin:

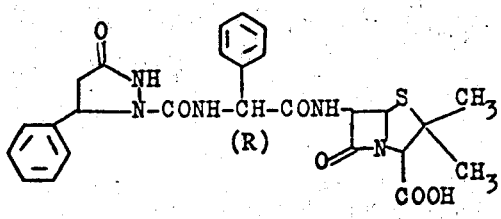

or the sodium salt thereof.
D(-)-α-[(2,4-Dimethyl-3-oxo-pyrazolidin-1-yl)-carbonylamino]-benzylpenicillin:

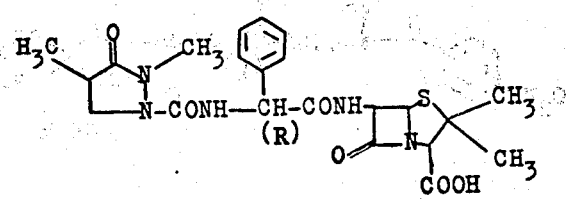

or the sodium salt thereof.
D(-)-α-[(1,4-Dimethyl-3-oxo-pyrazolidin-2-yl)-carbonylamino]-benzylpenicillin:

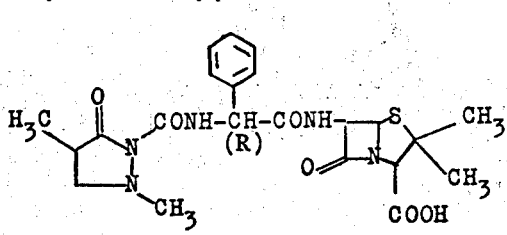

or the sodium salt thereof.
D(-)-α-[(2,5-Dimethyl-3-oxo-pyrazolidin-1-yl)-carbonylamino]-benzylpenicillin:

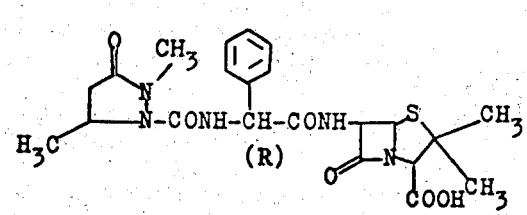

or the sodium salt thereof.
D(-)-α-[(1,5-Dimethyl-3-oxo-pyrazolidin-2-yl)-carbonylamino]-benzylpenicillin:

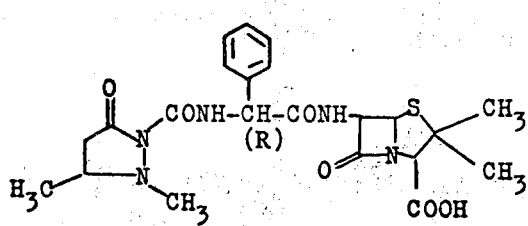

or the sodium salt thereof. D(-)-α-[(2-Methyl-3-oxo-5-phenyl-pyrazolidin-1-yl)-carbonylamino]-benzylpenicillin:

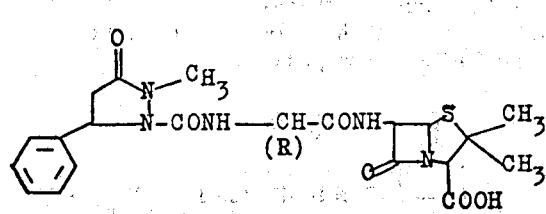

or the sodium salt thereof.
D(-)-α-[(1-Methyl-3-oxo-5-phenyl-pyrazolidin-2-yl)-carbonylamino]-benzylpenicillin:

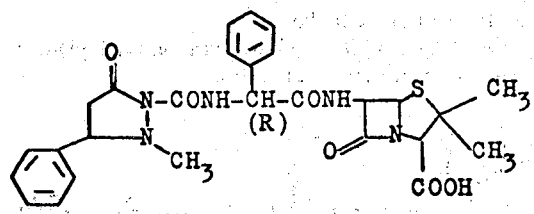

or the sodium salt thereof.
D(-)-α-[(1-Methyl-3-oxo-pyrazolidin-2-yl)-carbonylamino]-benzylpenicillin:

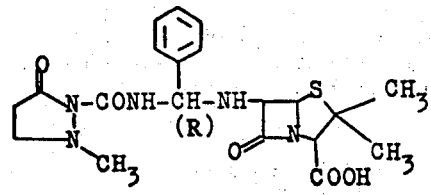

or the sodium salt thereof.
D(-)-α-[(3-Oxo-1,2-diaza-cyclohexan-1-yl)-carbonylamino]-benzylpenicillin:

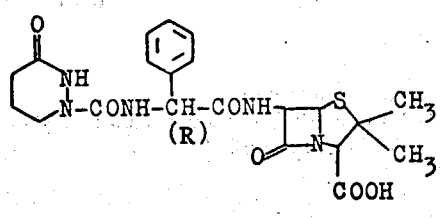

or the sodium salt thereof.
D(-)-α-[(3-Methyl-5-oxo-1,2,4-triazolin(3)-2-yl)-carbonylamino]-benzylpenicillin:

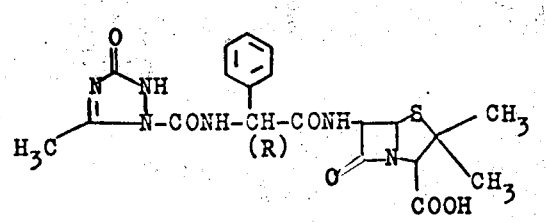

or the sodium salt thereof.
D(-)-α-[(3-Ethyl-5-oxo-1,2,4-triazolin(3)-2-yl)-carbonylamino]-benzylpenicillin:

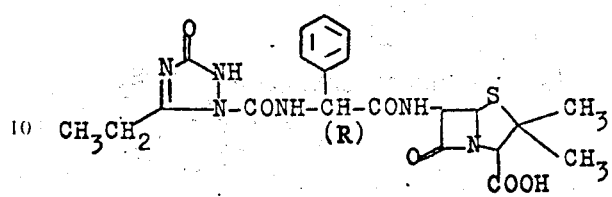

or the sodium salt thereof.
D(-)-α-[(3-Phenyl-5-oxo-1,2,4-triazolin(3)-2-yl)-carbonylamino]-benzylpenicillin:

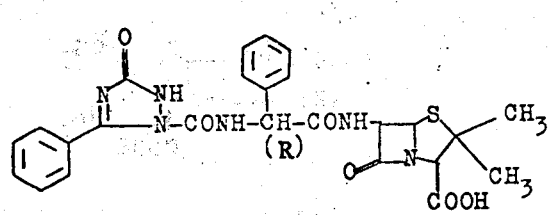

or the sodium salt thereof.
D(-)-α-[(4-Methyl-3,5-dioxo-1,2,4-triazolidin-1-yl)-carbonylamino]-benzylpenicillin:

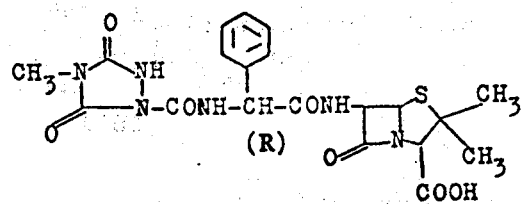

or the sodium salt thereof.
D(-)-α-[(4-Ethyl-3,5-dioxo-1,2,4-triazolidin-1-yl)-carbonylamino]-benzylpenicillin:

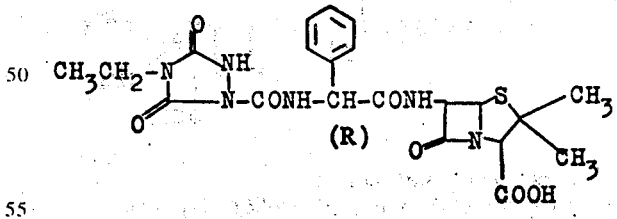

or the sodium salt thereof.
D(-)-α-[(4-Phenyl-3,5-dioxo-1,2,4-triazolidin-1-yl)-carbonylamino]-benzylpenicillin:

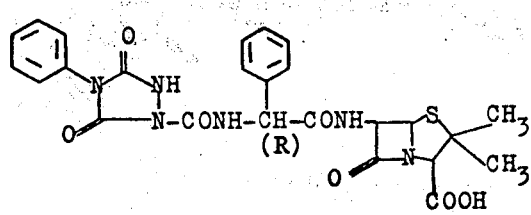

or the sodium salt thereof.

D(-)-α-[(4-Methyl-5-oxo-3-pyrazolidin-2-yl)-thiocarbonylamino]-benzylpenicillin:

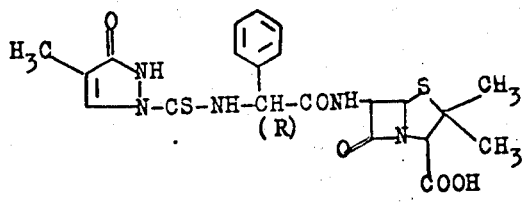

or the sodium salt thereof.

D(-)-α-[(4-Methyl-5-oxo-3-pyrazolin-2-yl)-thiocarbonylamino]-p-hydroxy-benzylpenicillin:

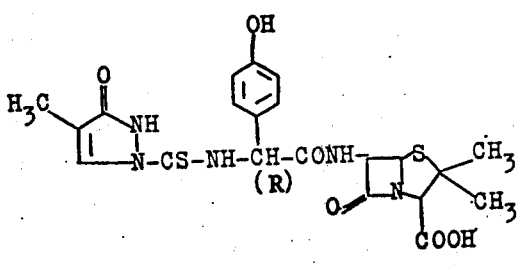

or the sodium salt thereof.

D(-)-α-[(4-Methyl-5-oxo-3-pyrazolin-2-yl)-thiocarbonylamino]-α-(cyclohexa-1,4-dien-1-yl)-methylpenicillin:

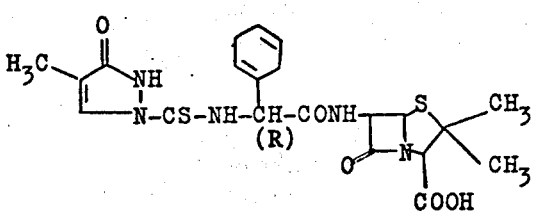

or the sodium salt thereof.

The pharmaceutical compositions of the present invention contain a major or minor amount e.g. 99.5 to 0.1%, preferably 95 to 0.5% of at least one penicillin as above defined in combination with a pharmaceutically acceptable non-toxic, inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from $25,000 - 1 \times 10^6$ U per kg of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and-/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose for oral and parenteral administration is $1.25 \times 10^6$ to $100 \times 10^6$ U of active ingredient.

The penicillins and their pharmaceutically acceptable nontoxic salts are useful not only for their broad anti-bacterial activity but also may be used for preventing systemic and topical bacterial infections and for treating such infections after they have occurred.

The present invention also comprises an animal feedstuff which comprises a nutritious material in combination with an anti-bacterially effective amount of a compound of the present invention. The present invention also includes the mixture of a compound of the present invention with animal fooder or drinking water in order to promote the growth of animals.

The present invention also includes pharmaceutical compositions which include one or more penicillins according to the present invention in combination with other penicillins such as, for example, Oxacillin, Dicloxacillin, Aminoglycooxidantibiotics such as Gentamicin, Kanamicin, Amikacin or Tobramicin thereby producing a still broader spectrum antibiotic composition.

According to both in vitro and in vivo data, the compounds of the present invention exhibit a strong anti-bacterial effect particularly against Pseudomonades.

The following results were obtained according to standard in vitro and in vivo tests.

The "in vitro" values were carried out as minimum inhibitory concentrations (MIC) in the test tube series dilution test in a liquid medium. The readings were taken after 24 hours' incubation at 37°C. The MIC is given by the non-cloudy test tube in the dilution series. It is quoted in U/ml of nutrient medium.

A whole medium of the following composition was used as the growth medium:

| | |
|---|---|
| Lab Lemco (Oxoid) | 10 g |
| Peptone (Difco) | 10 g |
| NaCl | 3 g |
| D(+) Dextrose (Merck) | 10 g |
| Buffer pH 7.4 | 1,000 ml |

The numbers here allotted to the penicillin compounds correspond to the numbers of the examples in which the preparation of the particular compound is described.

Table I

| Compound of Example No. | MIC [U/ml] | |
|---|---|---|
| | Pseudomonas Walter | Pseudomonas F 41 |
| 1 B | 8 | 8 |
| 2 C | 4 | 4 |
| 8 | 8 | 8 – 16 |
| 9 | 16 – 32 | 8 – 16 |
| 10 C | 8 – 16 | 8 – 16 |
| 11 C | 16 – 64 | 16 – 64 |
| 14 | 4 – 16 | 4 – 16 |
| Ampicillin | > 400 | > 400 |
| Carbenicillin | 200 | > 200 |

Using the test-tube dilution method, the penicillin compound of Example 1 B gave the following MIC values (in U/ml) against other bacteria:

| E.coli B | E.coli 26/6 | Proteus morg. | Proteus vulg. |
|---|---|---|---|
| 32 | 1 | 128 | 128 |

| Klebsiella pneum. | Staph.aureus 133 | Enterococcus ATCC 9790 |
|---|---|---|
| 128 | 0.5 | 32 |

The compounds of the invention are also active against other genera of bacteria. This is shown by the following experiment, which was carried out with the compound of Example 1.

The compound of Example 1 was diluted with 100 µg/ml with Muller-Hinton nutrient broth, with the addition of 0.1% of glucose. The nutrient solution in each case contained $1 \times 10^5$ to $2 \times 10^5$ bacteria per milliliter. The test tubes containing this mixture were incubated for 24 hours in each case and the degree of cloudiness was subsequently determined. Freedom from cloudiness indicates that the compounds are active. At a dosage of 100 µg/ml the following bacterial cultures were free of cloudiness:

E. coli 14; E. coli C 165; Proteus vulgaris 1017; Klebsiella K 10; Klebsiella 63; Salmonella sp.; Shigella sp.; Enterobacter sp.; Serratia sp.; Proteus, indole-negative, sp.; Proteus, indole-positive, sp.; Pasteurella pseudotuberculosis; Brucella sp.; Haemophilus influenzae; Bordetella bronchiseptica; Bacteriodes sp., Staphylococcus aureus 133; Neisseria catarrhalis sp.; Diplococcus pneumoniae sp.; Streptococcus pyogenes W; Enterococcus sp.; Lactobacillus sp.; Corynebacterium diphteriae gravis; Corynebacterium pyogenes M; Clostridium botulinium; Clostridium tetani; Borrelia sp.; Pseudomonas aeruginosa sp.; Aeromonas hydrophila sp.

Table 2 which follows shows the action of one of the penicillin compounds according to the invention against a series of bacteria in animal experiments with white mice. The white mice of strain CF₁ were infected intraperitoneally with the species of bacteria indicated in each case.

Table II

Animal experiments with white mice:
Determination of the ED$_{50}$ after 24 hours.

| Germ | Dose in units of the penicillin compound of Example 1 per kg, given subcutaneously |
|---|---|
| E. coli C 165 | 1 × 200,000 |
| Staphylococcus aureus | 1 × 40,000 |
| Pseudomonas aeruginosa W | 4 × 75,000 |
| Pseudomonas aeruginosa F 41 | 4 × 100,000 |

Therapy:
1 administration: 30 minutes after infection
4 administrations: 30 minutes, 2 hours, 4 hours and 6 hours after infection The ED$_{50}$ is a dose at which 50% of the infected animals still survive after 24 hours.

The α-aminobenzylpenicillin used in the examples which follow contained about 14% of water but anhydrous α-aminobenzylpenicillin [compare U.S. Pat. No. 3,144,445] can be used equally well.

The α-amino-p-hydroxybenzylpenicillin used in the examples contained about 13% of water, but anhydrous α-amino-p-hydroxybenzylpenicillin can be used equally well.

"Ampicillin" is α-aminobenzylpenicillin with the D(-)-=R- configuration in the side chain, "Amoxicillin" is α-amino-p-hydroxy-benzylpenicillin with the D(-)-= R- configuration in the side chain and "Epicillin" is α-amino-α-(1,4-cyclohexadien-1-yl)-methyl-penicillin with the D(-)-= R-configuration in the side chain.

The NMR spectra of the penicillin compounds were recorded in CD$_3$OD solution. The codes in brackets denote the following:

s = singlet          m = multiplet
d = doublet          AB = AB-system
t = triplet          J = coupling constant
q = quartet The IR spectra of the penicillin compound were recorded in Nujol suspension.

The following non-limitative examples more particularly illustrate the present invention.

EXAMPLE 1

(A) 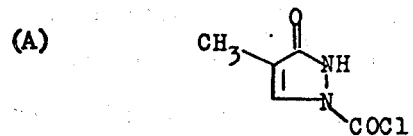

11 Parts by weight of phosgene were added, while stirring and cooling with ice, to a solution of 9.8 parts by weight of 4-methyl-5-oxo-pyrazoline-2 in 100 parts by volume of anhydrous tetrahydrofurane, the mixture was stirred for 30 minutes at 0°C and 1 hour at room temperature and again cooled to 0°C, 10.1 parts by weight of triethylamine were added dropwise over the course of 20 minutes and the mixture was stirred for a further 30 minutes at 0°C and then for 2 hours at room temperature. The triethylamine hydrochloride while precipitated was filtered off and washed with dry tetrahydrofurane and the combined solutions were evaporated to dryness in vacuo.

Crude yield: 15 parts by weight of 2-chlorocarbonyl-4-methyl-5-oxo-pyrazoline-3.

The crude product was recrystallized from acetone.
Yield: 5.5 parts by weight = 34% of theory; melting point = 169°C.

A further 1.8 parts by weight (11.2% of theory) of melting point = 155°C could be isolated from the mother liquor.

Calculated: C 37.4; H 3.1; Cl 22.1; N 17.4. Found: C 37.7; H 3.4; Cl 22.0; N 17.4.

IR bands at 3,120, 1,750, 1,628, 1,535, 875 and 790 cm⁻¹ (in Nujol).

NMR signals (in CDCl$_3$) at τ=0.05 (s, 1H); 2.2 (q, J∼1Hz, 1H) and 7.9 ppm (d, J∼1Hz, 3H).

(B) 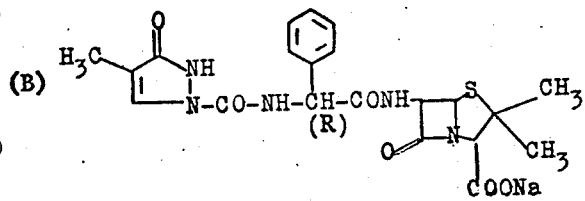

3.5 Parts by weight of 2-chlorocarbonyl-4-methyl-5-oxo-pyrazoline-3 were used in portions over the course of 15 minutes to a solution of 9.3 parts by weight of Ampicillin in 80 parts by volume of 80% strength aqueous tetrahydrofurane (pH = 8.2, adjusted with triethylamine), while cooling with ice and stirring, the pH being kept constant at between 7 and 8 by simultaneous addition of triethylamine.

The mixture was further stirred at room temperature until it was no longer necessary to add triethylamine to maintain the pH value of 6–7 (about 15 minutes). 50 Parts by volume of water were then added, the tetrahydrofurane was stripped off in vacuo on a rotary evaporator and the aqueous solution was extracted once with ethyl acetate, which was discarded, and then covered with fresh ethyl acetate, cooled to 0°C and acidified to pH 1.5 with dilute hydrochloric acid, while stirring vigorously. The ethyl acetate was separated off, the residue was extracted twice more with ethyl acetate and the combined ethyl acetate phases were washed with water and dried over MgSO$_4$. After filtration, about 23 parts by volume of a 1 molar solution of sodium 2-ethylhexanoate in ether containing methanol were added, the mixture was concentrated to a small volume in vacuo at room temperature and dissolved as rapidly as possible in the requisite amount of methanol, and the solution was poured into about 500 parts by volume of ice-cold ether, containing 10% of methanol, while stirring. The mixture was allowed to settle out for 30 minutes and the product was filtered off, again suspended in ether and again filtered off. The product was then dried for 2 days in vacuo in a desiccator over P$_2$O$_5$ and paraffin chips.

Yield: 100% of sodium D(-)-α-[(4-methyl-5-oxo-3-pyrazolin-2-yl)-carbonylamino]-benzylpenicillin.

β-Lactam content: 96%.

IR bands at 3,300, 1,755, 1,665, 1,598 and 1,370 cm⁻¹ (in Nujol).

NMR signals at τ=2.25 (s, 1H); 2.4–2.8 (m, 5H); 4.3 (s, 1H); 4.5 (AB, J = 4Hz, 2H); 5.8 (s, 1H); 8.0 (s, 3H); 8.45 (s, 3H) and 8.5 ppm (s, 3H).

EXAMPLE 2

(A)

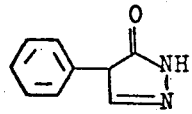

The product described in Offe at al. [Z. Naturforsch. 7b, 446 (1952)] was obtained in 91% yield by dropwise addition of hydrazine hydrate (3.75 parts by weight) to a solution of 13.4 parts by weight of α-formyl-phenylacetic ester in 25 parts by volume of THF at 0°C, followed by boiling for 2 hours under reflux, evaporation to dryness and recrystallization from ethanol. 4-Phenyl-5oxo-pyrazoline-2. Melting point = 231°C.

IR bands at 3,200, 3,105, 3,450–2,400, 1,612, 1,585, 1,515, 1,304, 1,277, 1,169 and 707 cm⁻¹ (in Nujol).

Calculated: C 67.4; H 5.0; N 17.5. Found: C 66.6; H 4.8; N 17.9.

(B)

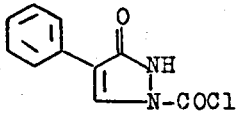

This was prepared from 9.6 parts by weight of 4-phenyl-5-oxo-pyrazolin-2 and 6.6 parts by weight of phosgene in the presence of triethylamine, as described in Example 1A. Instead of distilling the product, it was recrystallized from acetone/pentane.

Yield: 82% of 2-chlorocarbonyl-4-phenyl-5-oxo-pyrazoline-3.

Calculated: C 54.0; H 3.15; Cl 16.0; N 12.6. Found: C 54.2; H 3.2; Cl 14.2; N 12.3.

IR bands at 1,745, 1,715, 1,205, 881 and 766 cm⁻¹ (in Nujol).

(C)

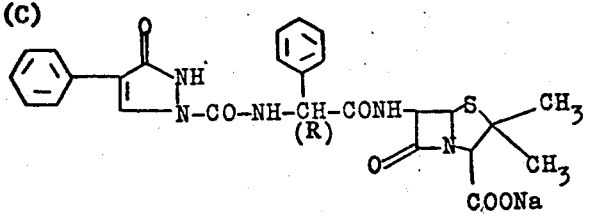

This was prepared from 6.5 parts by weight of 2-chlorocarbonyl-4-phenyl-5-oxo-pyrazoline-3 and 12.9 parts by weight of Ampicillin, as described in Example 1B.

Yield: 84% of sodium D(-)-α-[(4-phenyl-5-oxo-3-pyrazolin-2-yl)-carbonylamino]-penzylpenicillin.

Penicillin content: 93% (according to the NMR spectrum), 84% (according to analytical Craig distribution).

Calculated: *C 53.8; H 4.7; N 11.8; S 5.4. Found: C 53.3; H 4.9; N 11.6; S 6.0.

*(In the calculation, the presence of 3.9% of water, 1.1% of ether, 0.4% of ethyl acetate and 1.25% of sodium 2-ethyl-hexanoate, determined by NMR spectroscopy, was taken into account).

IR bands at 3,300, 1,772, 1,682, 1,615, 1,512, 1,320 and 1,260–1,220 cm⁻¹.

NMR signals at τ = 1.7 (s, 1H); 2.1–2.8 (m, 10H); 4.25 (s, 1H); 4.45 (AB, J = 4Hz, 2H); 5.75 (s, 1H) and 8.45 ppm (d, 8v = 2Hz, 6H).

EXAMPLE 3

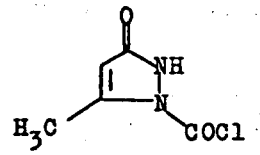

3-Methyl-5-oxo-pyrazoline-2 was reacted with phosgene, both in the presence of triethylamine as described in Example 1A, and also without catalyst a 40°–50°C (1 hour) in tetrahydrofurane. In both cases a solid which decomposed at about 250°C was obtained, which was insoluble in acetone and soluble in chloroform.

The analysis agreed with a mixture of 38% of 2-chlorocarbonyl-3-methyl-5-oxo-pyrazoline-3 and 62% of carbonyl-di-(3-methyl-5-oxo-2,5-dihydropyrazol-2-ide).

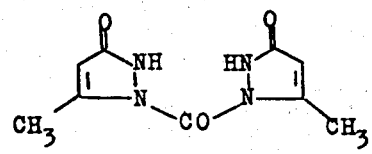

IR band at 1.780 cm⁻¹ (in Nujol).
Calculated: C 44.2; H 4.0; Cl 8.4; N 22.0. Found: C 44.0; H 3.2; Cl 8.1; N 19.2.

Reaction of the mixture with ampicillin, in the manner described in Example 1B, gave the following penicillin:

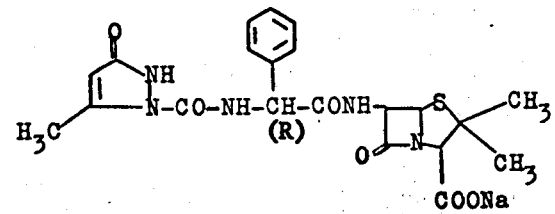

Calculated: *C 48.3; H 5.2; N 12.4; S 5.7. Found: C 48.3; H 5.4; N 12.3; S 6.4.

*(The presence of 1.2% methanol, 0.63% of ether, 5.9% of water and 4.4 % of sodium 2-ethylhexanoate, determined by NMR spectroscopy, was taken into account in the calculation).

Sodium D(-)-α-[(3-methyl-5-oxo-3-pyrazolin-2-yl)-carbonylamino]-benzylpenicillin.

IR bands at 3,300, 1,772, 1,710, 1,680, 1,608, 1,500 and 1,332 cm⁻¹.

NMR signals at τ=2.3–2.8 (m, 5H), 4.3 (s), 4.36 (s), 4.5 (AB, J = 4Hz) (a total of 4H); 5.8 (s, 1H); 7.5 (s, 3H), 8.4 (s) and 8.48 ppm (s) (a total of 6H).

β-Lactam content: 94% (iodometric determination), 88% (according to the NMR spectrum).

EXAMPLE 4

(A)

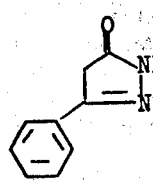

This was obtained from hydrazine hydrate and benzoylacetic ester by the procedure of Example 2A, the yield being 56% after recrystallization from ethanol: 3-phenyl-5-oxo-pyrazoline-2. Melting point = 238°C.

Calculated: C 67.5; H 5.0; N 17.5. Found: C 67.2; H 5.0; N 17.5.

IR bands at 3,400–2,000, 1,625, 1,598, 1,082, 943 and 750 cm$^{-1}$ (in Nujol).

(B)

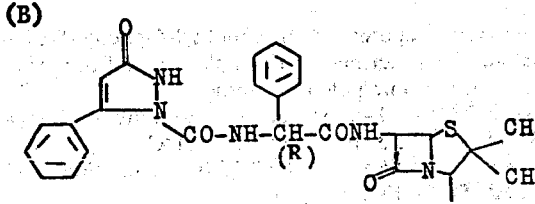

In order to produce the requisite carbonyl-bis-[3-phenyl-5-oxo-3-pyrazolinide-(2)] (a), the product of Example 4A was silylated and subsequently reacted with phosgene. The crude product was boiled with acetone. The residue showed a strong carbonyl band in the IR spectrum, at 1,790 cm$^{-1}$.

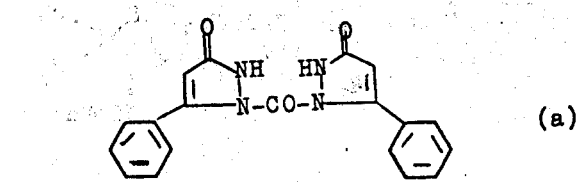

(a)

Calculated: C 65.9; H 4.0; N 16.2. Found: C 65.9; H 3.8; N 14.9.

Reaction with Ampicillin by the procedure of Example 1B gave sodium D(-)-α-[(3-phenyl-5-oxo-pyrazolin-(3)-2-yl)-carbonylamino]-benzylpenicillin in about 100% yield.

Penicillin content according to IR and NMR spectrum: 85–90%.

Calculated: (the presence of 4.4% of sodium ethylhexanoate and 4.2% of water, determined by NMR spectroscopy, was taken into account): C 53.3; H 4.8; N 11.4; S 5.2. Found: C 53.2; H 4.7; N 11.6; S 5.3.

IR bands at 1,770, 1,680, 1,605, 1,550 and 1,335 cm$^{-1}$.

NMR signals at $\tau$=2.1–2.9 (m, 11H); 4.3 (s), 4.54 (AB, J = 4Hz), (a total of 3H); 5.8 (s, 1H); 8.43 + 8.51 ppm (d, 6H).

EXAMPLE 5

(A)

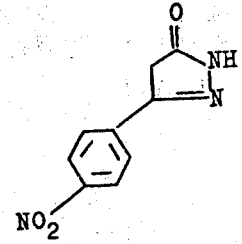

This was obtained from hydrazine hydrate and p-nitrobenzoylacetic ester by the procedure of Example 2A, the yield being 61% after recrystallization from ethanol. Melting point = 241°C. 3-(p-Nitrophenyl)-5-oxo-pyrazoline-2.

Calculated: C 52.7; H 3.4; N 20.5. Found: C 52.1; H 3.5; N 20.5.

IR bands at 3,370, 3,280, 3,110, 3,080, 1,603, 1,576, 1,512, 1,340, 1,120, 1,020, 865, 795 and 762 cm$^{-1}$ (in Nujol).

(B)

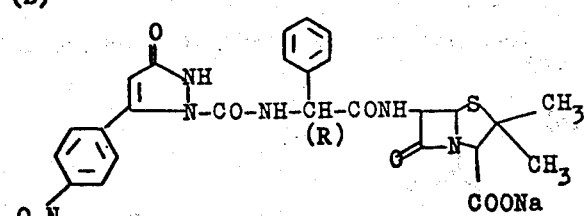

In order to prepare the requisite carbonyl-bis-[3-p-nitrophenyl-5-oxo-3-pyrazolinide-(2)] (a), the product of Example 5A was silylated and subsequently reacted with phosgene. The crude product first obtained was then boiled with acetone. The residue which remained showed a strong carbonyl band in the IR spectrum at 1,800 cm$^{-1}$.

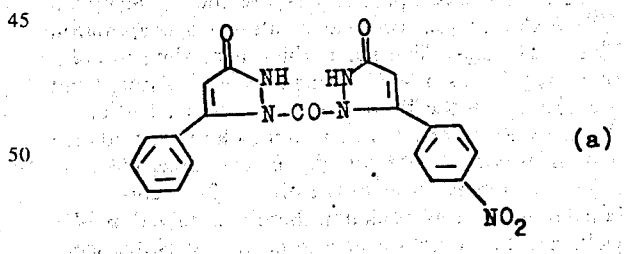

(a)

Calculated: C 52.2; H 2.8; Cl 0.0; N 19.3. Found: C 53.1; H 3.0; Cl 0.7; N 17.2.

Reaction with Ampicillin by the procedure of Example 1B gave sodium D(-)-α-[(3-p-nitrophenyl-5-oxo-pyrazolin(3)-2-yl)-carbonylamino]-benzylpenicillin in about 100% yield.

Penicillin content according to NMR and IR spectrum: 80–90%.

Calculated: (the presence of 8.2% of water, 2.0% of ethyl acetate, 2.0% of sodium ethylhexanoate and 0.8% of ether, determined by NMR spectroscopy, was taken into account): C 47.9; H 4.7; N 12.1; S 4.6. Found: C 47.3; H 4.7; N 12.1; S 4.6.

IR bands at 1,762, 1,678, 1,600, 1,520 and 1,345 cm⁻¹.

NMR signals at τ=1.8 + 2.05 (AB, J = 9Hz, 2H + 2H); 2.3–2.8 (m, 6H); 4.25 (s) 4.5 (AB, J = 4Hz), (a total of 3H); 5.75 (s, 1H); 8.4 + 8.5 ppm (d, 6H).

EXAMPLE 6

(A)

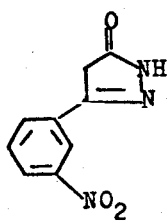

This was obtained from hydrazine hydrate and m-nitrobenzoylacetic ester by the procedure of Example 2A, the yield being 53% after recrystallization from ethanol.

Melting point: 270°C. 3-(m-Nitrophenyl)-5-oxo-pyrazoline-2.

Calculated: C 52.7; H 3.4; N 20.5. Found: C 51.4; H 3.4; N 20.1.

IR bands at 3,385, 1,585, 1,532, 1,022, 796 and 752 cm⁻¹.

(B)

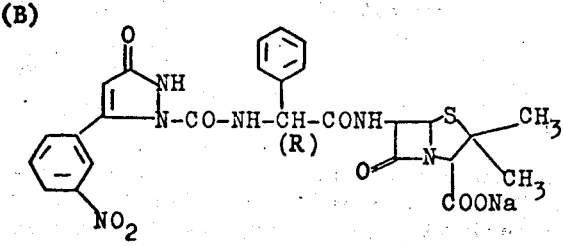

The requisite 2-chlorocarbonyl-3-m-nitrophenyl-5-oxo-pyrazoline-(3) was obtained from the product of Example 6A by silylation and subsequent reaction with phosgene, the crude product first obtained being boiled with acetone. The acetone solution on evaporation gave a non-crystalline solid which according to chlorine analysis was of 47% strength. Since a strong band was present in the IR spectrum at 1,810-1,730 cm⁻¹, the material was reacted with Ampicillin in accordance with the procedure of Example 1B. The sodium D(-)-α-[(3-m-nitrophenyl-5-oxo-pyrazolin(3)-2-yl)-carbonylamino]-benzylpenicillin thereby obtained in 14% yield had the structure according to the NMR spectrum.

Penicillin content according to IR and NMR spectrum about 90%.

IR bands at 3,280, 1,772, 1,717, 1,643, 1,525, 1,347 and 1,210 cm⁻¹.

NMR signals at τ = 1.5 (s, 1H); 1.9 (d, 2H); 2.3–3.0 (m, 7H); 4.3 (s), 4.5 (AB, J = 4Hz) (a total of 3H); 5.7 (s, 1H); 8.4 + 8.5 ppm (d, 6H).

EXAMPLE 7

(A)

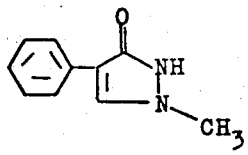

This was prepared from 14.8 parts by weight of α-formyl-phenylacetic ester and 3.9 parts by weight of methylhydrazine as described in Example 2A. It was recrystallized from acetone/ethanol. 2-Methyl-4-phenyl-5-oxo-pyrazoline-3. Melting point: 201°C. Yield: 81%.

IR bands at 3,300–1,800, 1,607, 1,553, 1,320, 1,260, 1,180, 948, 803, 778, 750 and 715 cm⁻¹ (in Nujol).

Calculated: C 69.0; H 5.8; N 16.1. Found: C 68.3; H 5.8; N 16.3.

NMR signals at τ = −0.35 (q, J ~ 1.3 Hz, 1H), 1.1–2.4 (m) and 2.23 (s) (a total of 3H); 2.5–3.1 (m, 3H) and 6.45 ppm (s, 3H).

(B)

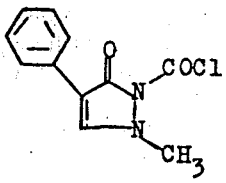

This was prepared from 2-methyl-4-phenyl-5-oxo-pyrazoline as described in Example 1A and recrystallized from benzene/petroleum ether.

Yield: 76% of 1-chlorocarbonyl-2-methyl-4-phenyl-5-oxo-pyrazoline-3, melting point 111°C.

Calculated: C 55.9; H 3.8; Cl 15.0; N 13.5. Found: C 56.3; H 4.0; Cl 13.3; N 12.3.

IR bands at 3,080, 1,779, 1,750, 1,680, 1,226, 1,206, 890, 781 and 697 cm⁻¹ (in Nujol).

NMR signals at τ =1.8 (s, 1H); 2.0–2.3 (m, 2H); 2.4–2.8 (m, 3H) and 6.33 ppm (s, 3H).

(C)

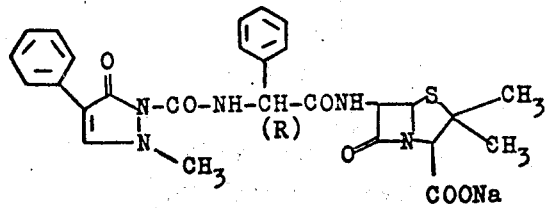

EXAMPLE 8

The compound was obtained in 61% yield from the product of Example 7B in the manner described in Example 1B.

Sodium D(-)-α-[(2-methyl-4-phenyl-5-oxo-3-pyrazolin-1-yl)-carbonylamino]-benzylpenicillin.

IR bands at 1,776, 1,762, 1,722, 1,605, 1,330 and 1,212 cm⁻¹.

NMR signals at τ = 2.3 (s, 1H); 2.4–2.75 (m, 10H); 4.4–4.65 (m, 3H); 5.7 (s, 1H) and 8.44 ppm (s, 6H).

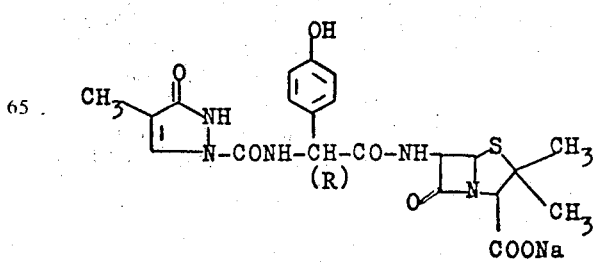

This was obtained in 94% yield from 2.0 parts by weight of Amoxicillin and 0.74 part by weight of the product of Example 1A, in the manner described in Example 1B.

Sodium D(-)-α-[(4-methyl-5-oxo-3-pyrazolin-2-yl)-carbonylamino]-p-hydroxybenzylpenicillin.

Penicillin content according to IR and NMR spectrum 90%.

IR bands at 3,300, 1,765, 1,720, 1,660, 1,605, 1,530 and 1,282 cm⁻¹.

NMR signals at τ = 2.3 (s, 1H); 2.7 + 3.2 (AB, J = 8.3 Hz, 2H + 2H); 4.49 (s), 4.52 (AB, J = 4Hz) (a total of 3H); 5.8 (s, 1H); 8.05 (s, 3H) and 8.43 + 8.48 ppm (d, 6H).

EXAMPLE 9

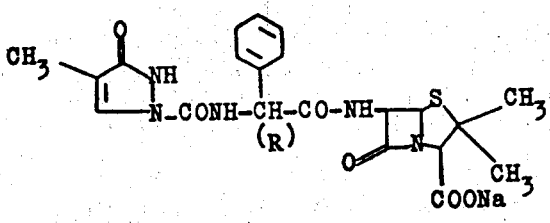

This was prepared in 71% yield from 1.25 parts by weight of D(-)-αamino-α-(cyclohexa-1,4-dien-1-yl)-methylpenicillin (Epicillin) and 0.6 part by weight of the product of Example 1A, in the manner described in Example 1B. Sodium D(-)-α-[(4-methyl-5-oxo-3-pyrazolin-2-yl)-carbonylamino]-α-(cyclohexa-1,4-dien-1-yl)-methylpenicillin.

Penicillin content according to IR and NMR spectrum ~90%.

IR bands at 1,767, 1,665, 1,607, 1,515, 1,320, 1,217 and 976 cm⁻¹.

NMR signals at τ = 2.33 (s, 1H); 4.1 (s, 1H); 4.3 (s, 2H); 4.5 (s, 2H); 5.0 (s, 1H); 5.8 (s, 1H); 7.27 (s, 4H); 8.05 (s, 3H) and 8.35 + 8.43 ppm (d, 6H).

EXAMPLE 10

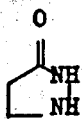

This was prepared analogously to the literature data (Ber. 84, 10 (1951) from acrylic ester and hydrazine hydrate. Oil. Pyrazolidin-3-one.

Calculated: C 41.9; H 7.0; N 32.5. Found: C 40.7; H 6.9; N 32.5.

IR bands at 3,200, 2,950, 1,725-1,640, 1,400, 1,304 and 1,198 cm⁻¹ (undiluted material).

NMR signals in CDCl₃ at τ = 4.1 (s, 2H); 6.45 (t, 2H) and 7.45 ppm (t, 2H).

(B)

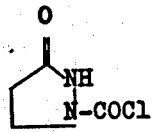

A mixture, cooled to 0°C, of 10 parts by weight of pyrazolidinone-3, 30 parts by volume of water, 17 parts by weight of NaHCO₃ and 20 parts by weight of phosgene in 200 parts by volume of chloroform was vigorously stirred for 15 minutes, the chloroform was separated off and the aqueous phase was again thoroughly stirred with 200 parts by volume of chloroform. The combined chloroform phases were dried over MgSO₄, the solvent was stripped off in vacuo and the product was recrystallized from acetone/petroleum ether.

Yield: 0.5 part by weight of 1-chlorocarbonyl-3-oxo-pyrazolidine, 2.9%, melting point = 180°C.

Calculated: C 32.3, H 3.4, Cl 23.9, N 18.8. Found: C 32.7, H 3.4, Cl 21.9, N 19.0.

IR bands at 3,180, 1,754, 1,700, 1,340, 1,307, 1,212, 992 and 776 cm⁻¹ (in Nujol).

A second fraction of melting point = 172°C was isolated in 15% yield by evaporating the aqueous phase and recrystallizing the residue from acetone/petroleum ether.

(C)

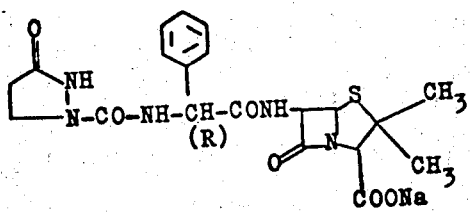

This was prepared in 35% yield from Ampicillin and the product of Example 10B, in the manner described in Example 1B.

Sodium D(-)-α-[(3-oxo-pyrazolidin-1-yl)-carbonylamino]-benzylpenicillin.

Penicillin content according to NMR and IR spectrum 90%.

IR bands at 3,300, 1,770, 1,665, 1,605, 1,530, 1,330 and 1,240 cm⁻¹.

NMR signals at τ = 2.4–2.8 (m, 5H); 4.5 (s); 4.53 (AB, J = 4Hz) (a total of 3H); 5.83 (s), 6.0 (t, J = 8Hz) (a total of 3H); 7.4 (t, J = 8Hz, 2H); 8.4 + 8.5 pp, (d, 6H).

EXAMPLE 11

(A)

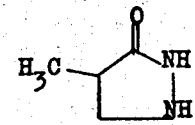

This was prepared according to Ber. 84, 10 (1951) from methacrylic acid methyl ester and hydrazine hydrate. Oil. Boiling point₀.₁ = 109°–110°C. 4-Methylpyrazolidin-3-one.

Calculated: C 44.5, H 7.4, N 25.9. Found: C 45.7, H 7.8, N 27.1.

IR bands at 3,200, 2,950, 2,880, 1,720–1,640, 1,460, 1,382, 1,305 and 935 cm⁻¹.

NMR signals at τ = 3.1 (very broad signal, 2H); 6.4 (q, 1H); 6.8-7.7 (m, 2H) and 8.9 ppm (d, J = 6Hz, 3H).

(B)

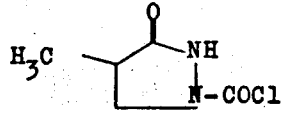

10.8 Parts by weight of 4-methyl-pyrazolidin-3-one were initially introduced into 100 parts by volume of tetrahydrofurane, 10.9 parts by weight of phosgene in 20 parts by volume of tetrahydrofurane were added dropwise at 0°C, the mixture was stirred for 30 minutes at 0°C, 10.1 parts by weight of triethylamine were then added dropwise, the mixture was stirred for 30 minutes at 0°C and 1 hour at room temperature and filtered, the filtrate was evaporated to dryness and the product was recrystallized from acetone, filtered off and washed with ether.

Yield: 34% of 1-chlorocarbonyl-3-oxo-4-methyl-pyrazolidine, melting point = 145°C.

Calculated: C 37.0, H 4.3, Cl 21.8, N 17.2. Found: C 37.4, H 4.4, Cl 21.3, N 16.6.

IR bands at 3,270–2,400, 1,735, 1,318, 990 and 788 cm$^{-1}$ (in Nujol).

(C)

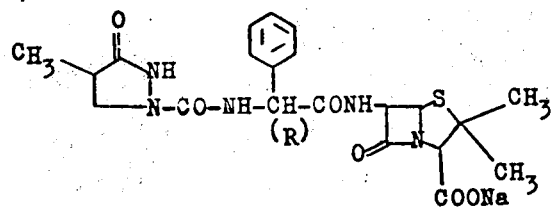

This was prepared from 5.2 parts by weight of 1-chlorocarbonyl-3-oxo-4-methyl-pyrazolidine and 14.1 parts by weight of Ampicillin as described in Example 1B.

A part of the product was obtained as free penicillic acid, which was sparingly soluble in ethyl acetate and water and which was converted into the sodium salt of the penicillin by dissolving in dimethylacetamide, adding sodium ethylhexanoate and precipitating the product with ether. Yield 42% of sodium D(-)-α-[(3-oxo-4-methyl-pyrazolidin-1-yl)-carbonylamino]-benzyl-penicillin.

A further fraction of the sodium salt was obtained from the ethyl acetate extract (as in Example 1B).

Yield: 38%.

Calculated: (the presence of 3.6% of water, 2.2% of ether and 0.7% of sodium 2-ethylhexanoate, determined by NMR spectroscopy, was taken into account in the calculation): C 49.1, H 5.3, N 13.2, S 6.0. Found: C 48.4, H 5.4, N 13.6, S 6.1.

IR bands at 1,765, 1,680–1,600, 1,520, 1,320 and 1,230 cm$^{-1}$.

NMR signals at $\tau = 2.4–2.8$ (m, 5H); 4.44 (s, 1H); 4.5 (AB, J = 4Hz, 2H); 5.4–5.8 (m), 5.8 (s) (a total of 2H); 6.2–6.7 (m, 1H); 6.9–7.5 (m, 1H); 8.5 (d, 6H) and 8.85 ppm (d, J = 6.5 Hz, 3H).

EXAMPLE 12

(A)

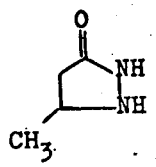

This was prepared according to Ber. 84, 10 (1951) from crotonic acid ethyl ester and hydrazine hydrate.

Boiling point$_{0.1}$ = 112°C. 5-Methyl-pyrazolidin-3-one.

Calculated: C 44.5, H 7.4, N 25.9. Found: C 46.5, H 7.8, N 25.3.

IR bands at 3,180, 2,970, 2,905, 2,830, 1,710–1,650, 1,346, 1,003 and 844 cm$^{-1}$ (in Nujol).

NMR signals at $\tau = 3.2$ (very broad signal, 2H); 6.2 (m, 1H); 7.4 (q, J$_1$ = 16Hz, J$_2$ = 7Hz, 7.8 (q, J$_1$ = 16Hz, J$_2$ = 8Hz) (a total of 2H) and 8.7 ppm (d, J = 6Hz, 3H).

(B)

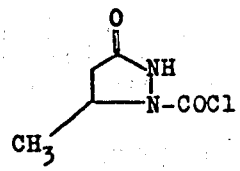

This was prepared as described in Example 11B from 10.8 parts by weight of 5-methyl-pyrazolidin-3-one. Recrystallization from acetone. 1-Chlorocarbonyl-3-oxo-5-methyl-pyrazolidine. Melting point = 143°C. Yield: 39%.

Calculated: C 36.9, H 4.3, Cl 21.9, N 17.2. Found: C 37.5, H 4.4, Cl 21.6, N 17.2.

IR bands at 3,300–2,200 and 1,760–1,640 cm$^{-1}$ (in Nujol).

(C)

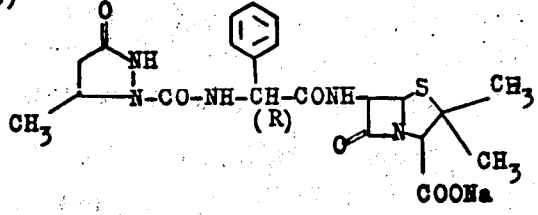

This was prepared in 94% yield from 6.1 parts by weight of 1-chlorocarbonyl-3-oxo-5-methyl-pyrazolidine and 16.5 parts by weight of Ampicillin, as described in Example 1B.

Sodium D(-)-α-[(3-oxo-5-methyl-pyrazolidin-1-yl)-carbonylamino]-benzylpenicillin.

Penicillin content according to NMR and IR spectrum: 90%.

Calculated: (the presence of water (3.3%), sodium ethyl-hexanoate (2.5%), ether (2.3%) and methanol (1.3%) determined by NMR spectroscopy, was taken into account in the calculation): C 49.3, H 5.4, N 12.8, S 5.8. Found: C 47.7, H 5.4, N 12.8, S 6.0.

IR bands at 1,770, 1,700–1,600, 1,522, 1,335 and 1,255 cm$^{-1}$.

NMR signals at $\tau = 2.4–2.8$ (m, 5H); 4.47 (s), 4.5 (AB, J = 4Hz), (a total of 3H); 4.9–5.6 (m, 1H); 5.8 (s, 1H); 6.8–7.4 (m, 1H); 7.9 (d, 1H); 8.4 (s, 3H); 8.5 (s, 3H) and 8.7 ppm (d, J = 6Hz, 3H).

EXAMPLE 13

(A)

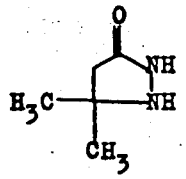

This was prepared according to Ber. 84, 10 (1951) from β-dimethylacrylic acid ethyl ester. Boiling point$_{0.1}$ = 103°–105°C. The substance crystallized after some hours. 5,5-Dimethyl-pyrazolidin-3-one. Melting point = 61°–62°C.

Yield: 82%.

Calculated: C 52.7, H 8.8, N 24.6. Found: C 52.9, H 8.9, N 24.7.

IR bands at 3,180, 1,675, 1,289, 1,275, 1,145, 1,038, 1,010, 983, 899 and 801 cm$^{-1}$ (in Nujol).

NMR signals at $\tau$ = 3.5 (broad signal, 2H); 7.6 (s, 2H) and 8.65 ppm (s, 6H).

(B)

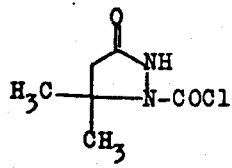

This was obtained from 5,5-dimethyl-pyrazolidin-3-one as described in Example 11B, the yield being 74% after recrystallization from benzene/petroleum ether. 1-Chlorocarbonyl-3-oxo-5,5-dimethyl-pyrazolidine. Melting point = 160°C.

Calculated: C 40.8, H 5.1, Cl 20.1, N 15.9. Found: C 41.5, H 5.3, Cl 20.1, N 15.7.

IR bands at 3,250–2,250, 1,750, 1,725–1,690, 1,332, 1,290, 1,180 and 800 cm$^{-1}$ (in Nujol).

(C)

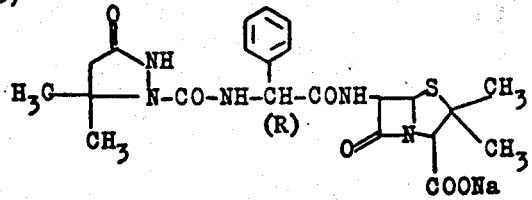

This was prepared as described in Example 1B from 8.8 parts by weight of 1-chlorocarbonyl-3-oxo-5,5-dimethyl-pyrazolidine and 21.4 parts by weight of Ampicillin.

Sodium D(-)-α-[(3-oxo-5,5-dimethyl-pyrazolidin-1-yl)-carbonylamino]-benzylpenicillin.

Yield: 86%

Penicillin content according to NMR and IR spectrum:

Calculated: (the presence of water (2.5%) and ether (2.3%), determined by NMR spectroscopy, was taken into account): C 50.6, H 5.5, N 13.0, S 6.0. Found: C 50.0, H 6.1, N 12.8, S 6.0.

IR bands at 3,300, 1,770, 1,700, 1,615, 1,520, 1,305 and 1,180 cm$^{-1}$.

NMR signals at $\tau$ = 2.3–2.8 (m, 5H); 4.5 (AB, J = 4Hz) and 4.55 (s) (a total of 3H); 5.8 (s, 1H); 7.3 (s, 2H); 8.4 (s), 8.5 (s), and 8.52 ppm (s) (a total of 12H).

EXAMPLE 14

A)

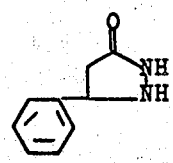

This was prepared according to Ber. 84, 10 (1951) from cinnamic acid ethyl ester and recrystallized from benzene and subsequently from isopropanol. 5-Phenyl-pyrazolidin-3-one.

Yield: 51%. Melting point = 104°C.

Calculated: C 66.7, H 6.2, N 17.3. Found: C 66.1, H 6.4, N 17.3.

IR bands at 3,600–2,500, 3,160, 1,710, 1,660, 1,080, 966, 943 and 707 cm$^{-1}$ (in Nujol).

NMR signals at $\tau$ = 2.66 (s, 5H); 5.3 (t, J approx. 8.5 Hz, 1H); 7.3 (2 d, J$_1$ = 7.8 Hz, J$_2$ =9.2 Hz, 2H).

(B)

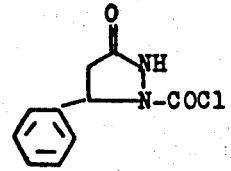

This was prepared as described in Example 11B from 5-phenyl-pyrazolidin-3-one. 1-Chlorocarbonyl-3-oxo-5-phenyl-pyrazolidine, obtained in 74% yield, melted at 146°C and showed the correct analysis.

Calculated: C 53.5, H 4.4, Cl 15.8, N 12.5. Found: C 54.1, H 5.0, Cl 15.3, N 12.5.

IR bands at 3,200–2,300, 1,740–1,688, 1,332, 1,244, 1,182, 990, 824 and 707 cm$^{-1}$ (in Nujol).

(C)

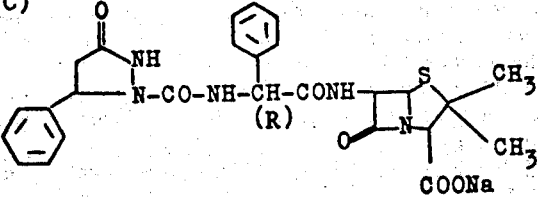

This was prepared as described in Example 1B from 11.2 parts by weight of 1-chlorocarbonyl-3-oxo-5-phenyl-pyrazolidine and 21 parts by weight of Ampicillin.

Yield: 82% of sodium D(-)-α-[(3-oxo-5-phenyl-pyrazolidin-1-yl)-carbonylamino]-benzylpenicillin.

Calculated: (the presence of water (3.5%), ether (1.3%) and methanol (0.9%), determined by NMR spectroscopy, was taken into account): C 53.9, H 5.1, N 11.8, S 5.4. Found: C 53.0, H 5.6, N 11.8, S 5.4.

IR bands at 3,275, 1,765, 1,660 and 1,607 cm$^{-1}$.

NMR signals at $\tau$ = 2.3–2.9 (m, 10H); 4.1–4.6 (m, 4H); 5.8 (s, 1H); 6.4–7.0 (m, 1H); 7.3–7.8 (m, 1H); and 8.4 ppm (d, 6H).

EXAMPLE 15

(A)

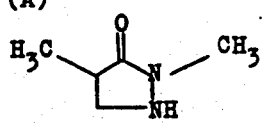 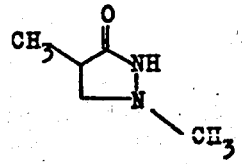

I  II

This was prepared analogously to Example 10A from 10.0 parts by weight of methacrylic ester and 5.5 parts by weight of methylhydrazine. Boiling point$_{0.4}$ = 112°–114°C.

Yield: 84% of 1,4- and 2,4-dimethyl-5-oxo-pyrazolidine.

Calculated: C 52.7, H 8.8, N 24.6. Found: C 49.5?, H 9.0, N 24.7.

IR bands at 3,700-2,500, 3,200, 2,970, 2,940, 2870 and 1,684 cm$^{-1}$ (undiluted material).

The N—CH$_3$ signals at 6.9τ (I) and 7.35τ (II) in the NMR spectrum indicate a mixture of 12% of I and 88% of II.

NMR signals at τ = 1.5 (very broad signal, integration not meaningful); 6.2–6.7 (m, 1H); 6.7–7.6 (m) and 6.9 (s) and 7.35 (s) (a total of 5H) and 8.8 ppm (d, J = 6Hz, 3H).

Calculated: (the presence of water (2.8%), ether (0.75%) and sodium ethylhexanoate (2.9%), determined by NMR spectroscopy, was taken into account): C 50.6, H 5.5, N 12.8, S 5.9. Found: C 50.4, H 6.2, N 12.9, S 6.3.

IR bands at 3,255, 1,770, 1,755, 1,718, 1,654, 1,610, 1,510 and 1,240 cm$^{-1}$.

NMR signals at τ = 2.4–2.8 (m, 5H); 4.3–4.6 (m, 3H); 5.8 (s, 1H); 6.2–7.0 (m), 6.85 (s), 7.25 (s), 7–7.6 (m) (a total of 6H); 8.4 (s) and 8.5 (s) (a total of 6 H); and 8.7–9.0 ppm (m, 3H).

The integration of the two N–CH$_3$ signals at τ = 6.85 (I) and 7.25 (II) indicates a ratio I:II of 1:3.

(B)

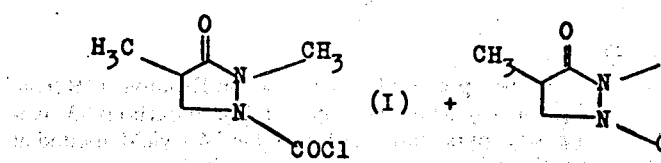

This was obtained as an oily product, in 87% yield, from the mixture, obtained in Example 15A, of 1,4- and 2,4-dimethyl-5-oxo-pyrazolidine, as described in Example 11B, after stirring for a further 3 hours at room temperature. Mixture of 1,4-dimethyl-2-chlorocarbonyl-5-oxo-pyrazolidine (I) and 2,4-dimethyl-1-chlorocarbonyl-5-oxo-pyrazolidine (II). The crude product gave the correct penicillin after reaction with Ampicillin.

IR bands at 2,970, 2,880, 1,808, 1,735, 1,460, 1,408, 1,272, 1,254, 1,211, 1,122, 848 and 788 cm$^{-1}$.

(C)

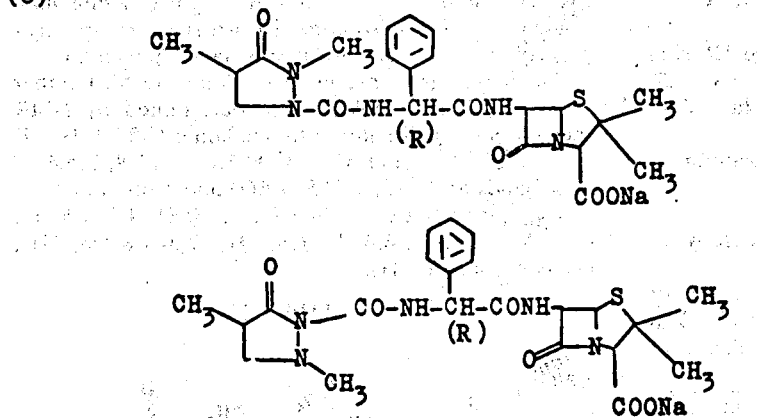

This was obtained from 9 parts by weight of the mixture of substances obtained in Example 15B and 20.2 parts by weight of Ampicillin.

Yield: 44% of a mixture of sodium D(-)-α-[(1,4-dimethyl-5-oxo-pyrazolidin-2-yl)-carbonylamino]-benzylpenicillin (I) and sodium D(-)-α-[(2,4-dimethyl-5-oxo-pyrazolidin-1-yl)-carbonylamino]-benzylpenicillin (II).

Penicillin content according to IR and NMR spectrum 80–90%.

EXAMPLE 16

(A)

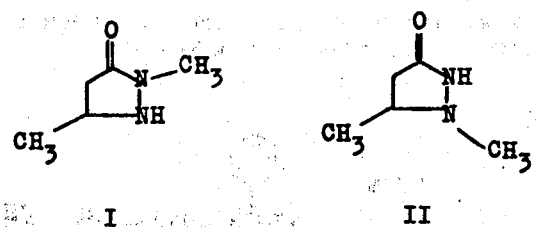

This was prepared analogously to Example 10A from 11.4 parts by weight of crotonic acid ethyl ester and 5.5 parts by weight of methylhydrazine.

Boiling point$_{0.1}$ = 87°C.

Yield: 91% of a mixture of 1,3-dimethyl-5-oxo-pyrazolidine (I) and 2,3-dimethyl-5-oxo-pyrazolidine (II).

Calculated: C 52.7, H 8.8, N 24.6. Found: C 52.2, H 8.7, N 24.5.

IR bands at 3,150, 2,970, 2,870, 1,680 and 1,460–1,340 cm⁻¹.

NMR signals at τ = 1.5 (very broad signal, 1H); 6.0–8.1 (m), 6.95 (s), 7.4 (s) (a total of 6H) and 8.75 ppm (d, J = 6Hz, 3H).

The two N—CH₃ signals at τ = 6.95 (I) and 7.4 (II) in the NMR spectrum indicate a mixture of 20% of I and 80% of II.

B)

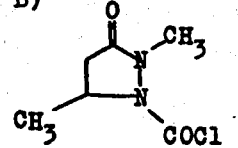 (I) 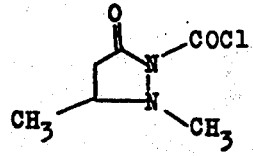 (II)

This was obtained in 84% yield as an oily product, from the mixture obtained in Example 16A, as described in Example 11B after stirring for 3 hours at room temperature.

Mixture of 1,3-dimethyl-2-chlorocarbonyl-5-oxo-pyrazolidine (I) and 2,3-dimethyl-1-chlorocarbonyl-5-oxo-pyrazolidine (II).

IR bands at 2,990, 2,955, 2,900, 1,804, 1,732 and 1,265 cm⁻¹.

This was obtained from 12 parts by weight of the product obtained in Example 16B and 28.2 parts by weight of Ampicillin, in the manner described in Example 1B.

Yield: 49% of a mixture of sodium D(-)-α-[(1,3-dimethyl-5-oxo-pyrazolidin-2-yl)-carbonylamino]-benzylpenicillin (I) and sodium D(-)-α-[(2,3-dimethyl-5-oxo-pyrazolidin-1-yl)-carbonylamino]-benzylpenicillin (II).

Penicillin content according to NMR and IR spectrum approx. 90%.

Calculated: (the presence of water (1.9%), ether (1.4%) and sodium ethylhexanoate (3.3%), determined by NMR spectroscopy, was taken into account): C 49.9, H 5.5, N 12.8, S 5.9. Found: C 49.0, H 5.5, N 12.4, S 6.0.

IR bands at 3,270, 1,758, 1,715, 1,667, 1,600 and 1,318 cm⁻¹.

NMR signals at τ = 2.3–2.9 (m, 10H); 4.2–4.6 (m, 3H); 5.4–5.7 (m, 0.4H, I); 5.8 (s, 1H); 6.2–7.5 (m), 6.8 (s, I), 7.2 (s, II), (a total of 5.6H) and 8.45 ppm (s, 6H).

The NMR spectrum indicates a 1.5:2.0 mixture of I and II.

EXAMPLE 17

(A)

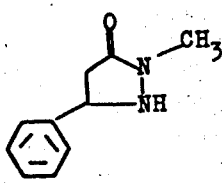 (I) + 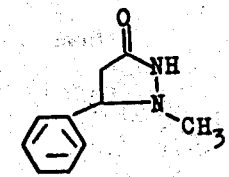 (II)

(C)

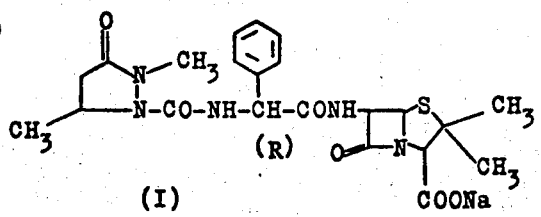

(I)

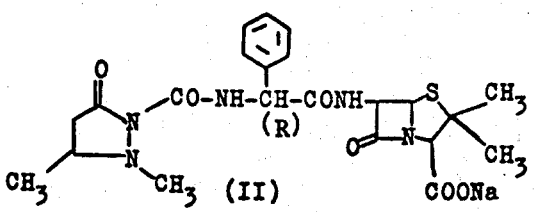

(II)

This was prepared analogously to Example 10A from 17.6 parts by weight of cinnamic acid ethyl ester and 5.5 parts by weight of methylhydrazine.

Boiling point₀.₁ = 139°C. Yield: 76% mixture of 1-methyl-3-phenyl-5-oxo-pyrazolidine (I) and 2-methyl-3-phenyl-5-oxo-pyrazolidine (II).

Calculated: C 68.7, H 6.3, N 16.0. Found: C 67.8, H 6.7, N 15.9.

IR bands at 3,550–2,500, 3,150, 2,970, 2,860, 1,675, 1,450, 1,340, 1,130, 762 and 705 cm⁻¹ (undiluted material)

NMR signals at τ = 2.4–2.9 (m, 5H); 6.1 (q, 1H); 6.8–7.7 (m, 2H); 6.9 (s, 0.6H, CH₃ of I) and 7.45 ppm (s, 2.4H, CH₃ of II).

The NMR spectrum indicates a 1:4 mixture of (I) and (II) (integration of the CH₃ signals).

(B)

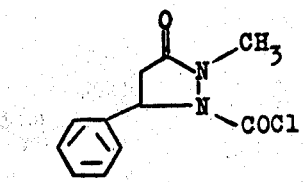 (I) 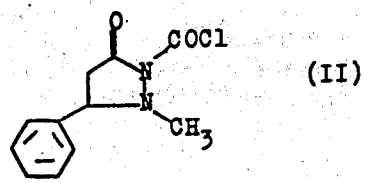 (II)

This was obtained as an oily product in 84% yield from the mixture of substances obtained in Example 17A, as described in Example 11B.

Mixture of 1-methyl-2-chlorocarbonyl-3-phenyl-5-oxo-pyrazolidine (I) and 1-chlorocarbonyl-2-methyl-3-phenyl-5-oxo-pyrazolidine (II).

IR bands at 2,995, 2,955, 2,900, 1,804, 1,740 and 1,260 cm⁻¹ (undiluted material).

(C)
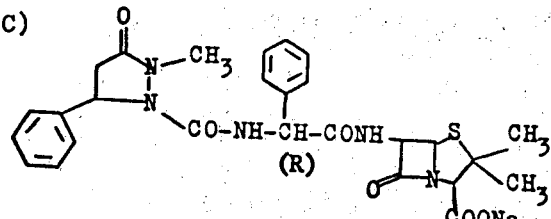
I

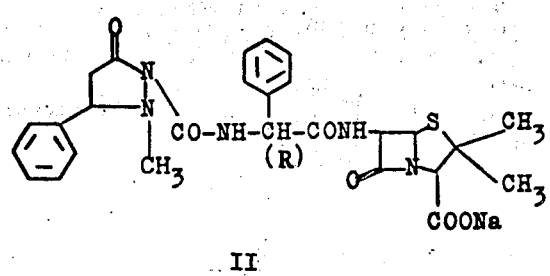
II

This was obtained in 69% yield in the manner described in Example 1B from Ampicillin and the product of Example 17B.

Mixture of sodium D(-)-α-[(1-methyl-3-phenyl-5-oxo-pyrazolidin-2-yl)-carbonylamino]-benzylpenicillin (I) and sodium D(-)-α-[(2-methyl-3-phenyl-5-oxo-pyrazolidin-1-yl)-carbonylamino]-benzylpenicillin (II).

Penicillin content according to NMR and IR spectrum approx. 90%.

Calculated: * H 5.3, N 11.4, S 5.3. Found: H 5.2, N 10.9, S 5.5.

*(The presence of 2.8% of sodium 2-ethylhexanoate, 2.0% of water and 1.2% of ether, determined by NMR spectroscopy, was taken into account).

IR bands at 3,280, 3,060, 3,040, 1,760, 1,600, 1,320 and 1,230 cm⁻¹.

NMR signals at τ= 2.3–2.9 (m, 10H); 4.2–4.6 (m, 3H); 5.4–5.7 (m, 0.4H, I); 5.8 (s, 1H); 6.2–7.5 (m), 6.8 (s, I), 7.2 (s, II) (a total of 5.6 H) and 8.45 ppm (s, 6H).

The integration ratio of the N—CH₃ signals at 6.8 and 7.2 indicates a ratio I:II = 1.5:2.0.

EXAMPLE 18

(A)
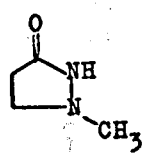

This was prepared in accordance with the literature instructions for pyrazolidinone (Ber. 84, 10 (1951) from acrylic ester and methylhydrazine. 24 hours refluxing. Boiling point₁ = 115°–120°C. Yield: 66% of 1-methyl-3-oxo-pyrazolidine, oil.

Calculated: C 48.0, H 8.0, N 28.0. Found: C 47.3, H 8.1, N 27.7.

NMR signals at τ= 3.9 (s, 1H); 6.75 (t, 2H); 7.4 (s) and 7.4 ppm (t) (a total of 5H) (in CD₃OD).

(B)
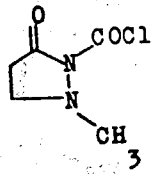

This was prepared in 23% yield from the product of Example 18A, analogously to Example 11B. The solid which remained after ether extraction of the crude product, and which did not have a sharp melting point, gave the correct penicillin in the pure form (see Example 18C).

1-Methyl-2-chlorocarbonyl-3-oxo-pyrazolidine.

IR bands at 1,798, 1,708, 1,180, 1,117, 1,063, 1,007, 800 and 686 cm⁻¹ (in Nujol).

(C)
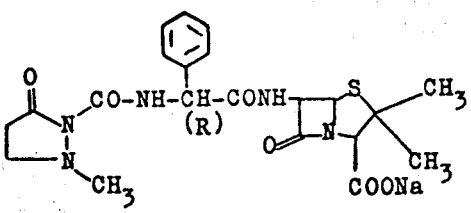

This was prepared from Ampicillin and the product of Example 18B in 52% yield (procedure of Example 1B). Sodium D(-)-α-[(1-methyl-3-oxo-pyrazolidin-2-yl)-carbonylamino]-benzylpenicillin.

Penicillin content 90% according to NMR and IR spectrum, 85% according to analytical Craig distribution.

Calculated: (the presence of 4.5% of water, 2.7% of sodium ethylhexanoate and 1.1% of ether, determined by NMR spectroscopy, was taken into account): C 48.5, H 5.1, N 12.8, S 5.9. Found: C 49.3, H 5.6, N 12.2, S 6.2.

IR bands at 3,300, 1,764, 1,725, 1,675, 1,610, 1,520, 1,340, 1,305 and 1,248 cm⁻¹.

NMR signals at τ = 2.4–2.8 (m, 5H); 4.4 (s), 4.55 (AB, J = 4Hz) (a total of 3H); 5.85 (s, 1H); 6.2–6.8 (m, 2H); 6.8–7.5 (m), 7.3 (s) (a total of 5H) and 8.43 + 8.5 ppm (d, 6H).

EXAMPLE 19

(A)
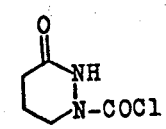

10 Parts by weight of 3-oxo-1,2-diazacyclohexane [prepared by heating 1 mol of β-chloropropionic acid ethyl ester with 1.3 mols of hydrazine hydrate for 3 hours, yield 75% boiling point₀.₀₄ = 80°–84°C, NMR signals in D₂O at τ= 6.5 (t, 2H) and 7.4–8.3 ppm (m, 4H)] in methylene chloride /tetrahydrofurane were mixed at 0°C with 10 parts by weight of phosgene and subsequently with 10 parts by weight of triethylamine and the mixture was stirred for 30 minutes at 0°C and overnight at room temperature. It was evaporated to dryness in vacuo, the residue was suspended in tetrahydrofurane, the suspension was filtered, the solvent was evaporated to ⅓, the triethylamine hydrochloride which precipitated was again filtered off and the filtrate was evaporated completely. The oily residue was additionally kept for some hours under an oil pump.

Yield: 100% of 1-chlorocarbonyl-3-oxo-1,2-diazacyclohexane.

Calculated: C 37.0, H 4.3, Cl 21.9, N 17.2.
Found: C 38.3, H 5.4, Cl 21.6, N 15.6.

IR bands at 3,160, 2,950, 1,820–1,680, 1,462, 1,410, 1,295, 1,260 and 1,162 cm⁻¹.

NMR signals at τ= 0.05 (s, 1H); 6.0–6.5 (m, 2H) and 7.3–8.3 ppm (m, 4H) (in CDCl₃).

(B)

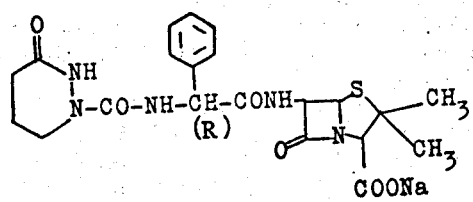

This was prepared according to the procedure of Example 1B in 30% yield from Ampicillin and the product from Example 19A.

Sodium D(−)-α-[(3-oxo-1,2-diazocyclohexan-1-yl)-carbonylamino]-benzylpenicillin.

Penicillin content according to NMR and IR spectrum approx. 70%.

IR bands at 3,300, 1,765, 1,665, 1,605, 1,540, 1,325 and 1,250 cm⁻¹.

NMR signals at τ= 2.3–2.8 (m, 5H); 4.52 (s), 4.53 (AB, J = 4Hz), (a total of 3H); 5.8 (s, 1H); 6.4 (t, 2H); 7.2–8.2 (m, 4H); 8.4 + 8.5 ppm (d, 6H).

EXAMPLE 20

(A)

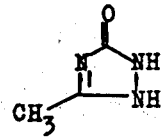

This was prepared analogously to the instructions given by Gehlen (Ann. 563, 185 (1949)).

32 Parts by volume of concentrated hydrochloric acid and 27.5 parts by weight of potassium cyanate in 50 parts by volume of water were added, while cooling, to 25 parts by weight of acetic acid hydrazide in 125 parts by volume of water, the mixture was stirred for 15 minutes, boiled with 20 parts by weight of KOH in 50 parts by volume of water for 1 hour, neutralized with concentrated hydrochloric acid and evaporated to dryness, and the residue was boiled with ethanol. The residue which remained after evaporating the ethanol was recrystallized from ethanol. Yield: 45% of 3-methyl-5-oxo-1,2,4-triazoline-3. Melting point = 248°C.

Calculated: C 36.4, H 5.1, N 42.5. Found: C 36.6, H 5.1, N 43.6.

NMR signals at τ= 5.0 (broad s, 2H) and 7.8 ppm (s, 3H).

(B)

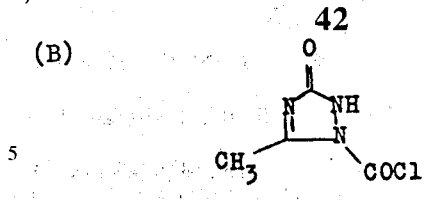

8.9 Parts by weight of methyltriazolone, 20 parts by weight of trimethylchlorosilane, 15 parts by weight of triethylamine and 50 parts by volume of dioxane were kept under reflux for 10 hours while stirring and excluding moisture; the mixture was filtered hot, the residue was eluted with 50 parts by volume of hot dioxane, 10 parts by weight of phosgene were added to the combined solutions and the mixture was stirred for 5 hours at room temperature and filtered. The filtrate was evaporated in vacuo and the residue was dried under an oil pump and recrystallized from chloroform. 1st fraction: Yield 2.3 parts by weight, decomposition point >155°C. Consisted of 45% of starting material and 55% of chlorocarbonylmethyltriazolone (analysis).

Calculated: for 55% of product and 45% of starting material: C 32.5, H 3.7, Cl 12.1, N 32.0. Found: C 32.7, H 3.7, Cl 11.2, N 33.3.

IR bands at 3,140, 1,830, 1,778, 1,730, 1,618, 1,340, 1,212, 1,040 and 805 cm⁻¹ (in Nujol).

2nd fraction: Yield: 2.5 parts by weight; consisted, according to the analysis, of ∼⅔ starting material and ∼⅓ 2-chlorocarbonyl-3-methyl-5-oxo-1,2,4-triazoline-3.

Calculated: for 66.5% of starting material and 33.5% of product: C 34.0, H 4.8, Cl 7.5, N 37.1. Found: C 34.1, H 4.2, Cl 7.6, N 37.4.

(C)

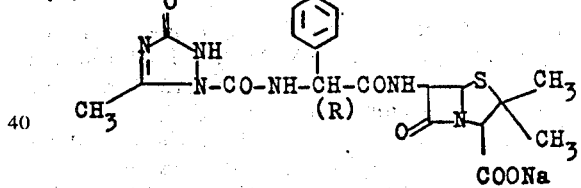

2 Parts by weight of the product from Example 20B (containing 55% of acid chloride) were added in portions to a solution of 5.7 parts by weight of Ampicillin in 50 parts by volume of 80% strength aqueous THF (pH kept at 7–8 with triethylamine); the mixture was further stirred until the pH was constant (approx. 15 minutes), the THF was stripped off in vacuo, the aqueous solution was extracted with 30 parts by volume of ethyl acetate, covered with fresh ethyl acetate and acidified to pH = 2 while cooling with ice, the organic phase was again separated off, the residue was again extracted with ethyl acetate, the combined ethyl acetate solutions were washed with water and dried over MgSO₄, 7 parts by volume of a one molar solution of sodium 2-ethylhexanoate in ether containing methanol were added, the mixture was evaporated in vacuo until it had an oily consistency and was then dissolved in a little methanol, and a 10-fold amount of ice-cold ether was added. After brief settling-out, the product was filtered off, washed with ether and dried in a desiccator over P₂O₅ paraffin chips.

Yield: 1.7 parts by weight of sodium D(−)-α-[(3-methyl-5-oxo-1,2,4-triazol-3-in-2-yl)-carbonylamino]-benzylpenicillin = 50% based on acid chloride employed.

Penicillin content according to NMR and IR spectrum 80–85%.

IR bands at 1,765, 1,680, 1,605, 1,530 and 1,330 cm⁻¹ (in Nujol).

NMR signals at τ = 2.4–2.85 (m, 5H); 4.33 (s), 4.5 (AB, J = 4Hz) (a total of 3H); 5.8 (s, 1H); 7.8 (s, 3H); 8.4 and 8.5 ppm (d, 6H).

EXAMPLE 21

(A)

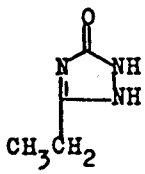

This was prepared according to Example 20A from propionic acid hydrazide and was twice recrystallized from isopropanol. Yield: 27% of 3-ethyl-5-oxo-1,2,4-triazoline-3, melting point = 214°C.

IR bands at 1,738, 1,596, 1,288, 1,060, 1,020, 975, 825, 785 and 728 cm⁻¹.

NMR signals at τ = 7.45 (q, 2H) and 8.7 ppm (t, 3H) (in CD₃OD).

(B)

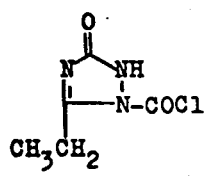

This was prepared as described in Example 20B from the product of Example 21A. Recrystallized from benzene. 2-Chlorocarbonyl-3-ethyl-5-oxo-1,2,4-triazoline-3. Yield: 35%, melting point = 169°C.

Calculated: C 34.2, H 3.4, Cl 20.2, N 24.0. Found: C 35.2, H 3.7, Cl 19.4, N 24.4.

IR bands at 3,180, 1,821, 1,765, 1,682, 1,610, 1,320, 1,298, 1,179, 1,150, 1,070, 1,035, 958, 910 and 792 cm⁻¹ (in Nujol).

(C)

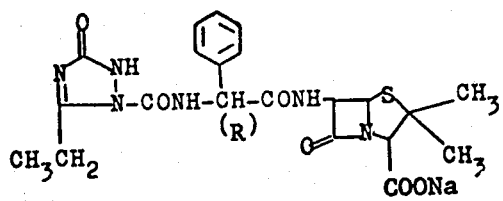

This was prepared in 92% yield in the manner described in Example 20C from Ampicillin and the compound from Example 21B.

Sodium D(-)-α-[(3-ethyl-5-oxo-1,2,4-triazol-3-in-2-yl)-carbonylamino]-benzylpenicillin.

Penicillin content according to NMR and IR spectrum 90%.

Calculated: (the presence of 4.0% of water 2.2% of ether, 1.8% of methanol and 1.0% of sodium ethylhexanoate, determined by NMR spectroscopy, was taken into account): C 47.6, H 5.2, N 15.0, S 5.7. Found: C 46.1, H 5.3, N 15.1, S 5.6.

IR bands at 3,220, 1,775, 1,760, 1,736, 1,680, 1,604, 1,510 and 1,322 cm⁻¹.

NMR signals at τ = 2.35–2.8 (m, 5H); 4.25 (s), 4.5 (AB, J = 4Hz) (a total of 3H); 5.8 (s, 1H); 7.4 (q, 2H); 8.4 + 8.45 (d, 6H) and 8.75 ppm (t, 3H).

EXAMPLE 22

(A)

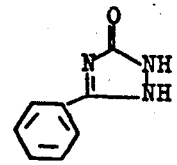

This was prepared from benzoic acid hydrazide as described in Example 20A. On acidifying, the product precipitated and was filtered off (melting point = 245°C) and recrystallized from aqueous alcohol (melting point = 248°C). Yield: 41% 3-Phenyl-5-oxo-1,2,4-triazol-3-ine.

Calculated: (water content 1 mol): C 53.7, H 5.0, N 23.5. Found: C 53.8, H 5.1, N 23.5.

IR bands at 3,415, 3,350–2,370, 1,645, 1,605, 1,536, 1,325, 1,228, 903 and 700 cm⁻¹ (in Nujol).

(B)

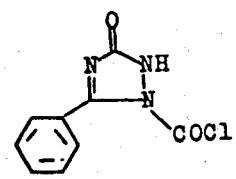

This was obtained in 13.5% yield in the manner described in Example 20B from the product of Example 22A after reprecipitation from benzene/pentane. Solid substance, decomposition point approx. 100°C. 2-Chlorocarbonyl-3-phenyl-5-oxo-1,2,4-triazol-3-ine.

IR bands (in Nujol) at 3,500–2,500, 1,830–1,770, 1,750–1,720, 1,615 and 1,305 cm⁻¹.

(C)

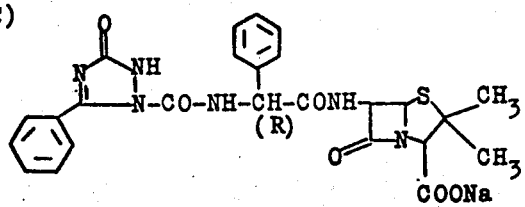

This was obtained in 45% yield from Ampicillin and the product of Example 22B (procedure of Example 20C). Sodium D(-)-α-[(3-phenyl-5-oxo-1,2,4-triazol-3-in-2-yl)-carbonylamino]-benzylpenicillin.

Penicillin content according to NMR and IR spectrum 80–85%.

NMR signals at τ = 2.6 (m, 10H); 4.4–4.7 (m, 3H); 5.8 (s, 1H) and 8.43 + 8.49 ppm (d, 6H).

EXAMPLE 23

(A)

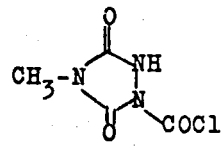

This was obtained from 4-methyl-3,5-dioxo-1,2,4-triazolidine (prepared according to Org. Synth. 51, 122) (yield 82%). (Procedure of Example 20B).

1-Chlorocarbonyl-4-methyl-3,5-dioxo-1,2,4-triazolidine.

IR: very strong band at 1,800–1,720 cm⁻¹.

(B)

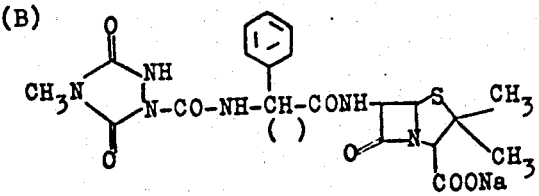

This was prepared in 75% yield from the product of Example 23A and Ampicillin by the procedure of Example 20C.

sodium D(-)-α-[(4-methyl-3,5-dioxo-1,2,4-triazolidin-1-yl)-carbonylamino]-benzylpenicillin.

Penicillin content according to IR and NMR spectrum: 80%.

Calculated: (the presence of 4% of ethyl acetate, 3% of sodium ethylhexanoate and 2.5% of water, determined by NMR spectroscopy, is taken into account): C 46.3, H 4.6, N 14.8, S 5.6. Found: C 45.7, H 4.6, N 14.2, S 6.0.

IR bands at 3,280, 1,770, 1,727, 1,632 and 1,532 cm⁻¹.

NMR signals at $\tau$ = 2.4–2.8 (m, 5H); 4.4 (s), 4.55 (AB, J = 4Hz) (a total of 3H); 5.8 (s, 1H); 7.05 (s, 3H) and 8.45 + 8.55 ppm (d, 6H).

EXAMPLE 24

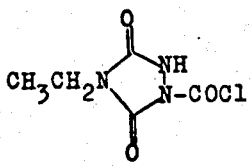

This was obtained in 34% yield from 4-ethyl-3,5-dioxo-1,2,4-triazolidine (prepared according to Org. Synth. 51, 122) as a solid of decomposition point 140°C. (Procedure of Example 20B).

1-Chlorocarbonyl-4-ethyl-3,5-dioxo-1,2,4-triazolidine.

Very strong IR band at 1,840–1,600 cm⁻¹ (in Nujol).

(B)

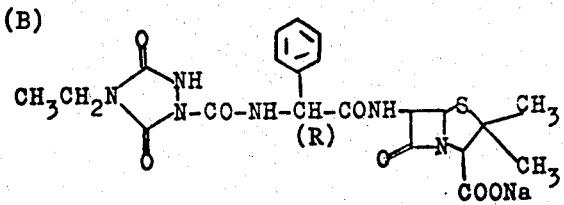

This was prepared in 80% yield from the product of Example 24A and Ampicillin by the procedure of Example 20C.

Sodium D(-)-α-[(4-ethyl-3,5-dioxo-1,2,4-triazolidin-1-yl)-carbonylamino]-benzylpenicillin.

Penicillin content according to IR and NMR spectrum 85%.

IR bands at 3,260, 1,760, 1,730–1,670, 1,625 and 1,532 cm⁻¹.

NMR signals at $\tau$ = 2.4–2.8 (m, 5H); 4.4 (s, 1H); and 4.5 (AB, J = 4Hz) (a total of 3H); 5.8 (s, 1H); 6.45 (q, 2H); 8.4 + 8.5 (d, 6H) and 8.8 ppm (t, 3H).

EXAMPLE 25

(A)

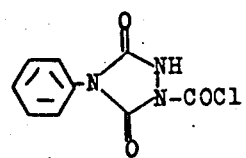

This was obtained in 77% yield from 4-phenyl-3,5-dioxo-1,2,4-triazolidine (prepared according to Org. Syn. 51, 122) after recrystallization from acetone/pentane (procedure of Example 20B). 1-Chlorocarbonyl-4-phenyl-2,5-dioxo-1,2,4-triazolidine. Decomposition point approx. 122°C.

Calculated: C 45.1, H 2.5, Cl 14.8. Found: C 45.4, H 3.0, Cl 13.6.

IR bands at 3,300–2,400, 1,780, 1,755, 1,712, 1,300, 1,270, 1,232, 1,106 and 770 cm⁻¹ (in Nujol).

(B)

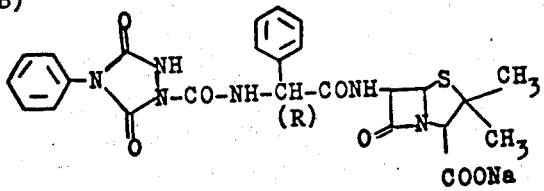

This was prepared in 69% yield from the product of Example 25A and Ampicillin according to the procedure of Example 20C.

Sodium D(-)-α-[(4-phenyl-3,5-dioxo-1,2,4-triazolidin-1-yl)-carbonylamino]-benzylpenicillin.

Calculated (the presence of 5.1% of ethyl acetate, 6.4% of sodium ethylhexanoate and 1.8% of water, determined by NMR spectroscopy, was taken into account): C 50.9, H 4.6, N 12.7, S 4.9. Found: C 49.2, H 5.0, N 12.3, S 5.3.

β-Lactam content according to NMR and IR spectrum approx. 85%.

IR bands at 3,270, 1,770, 1,720, 1,640, 1,530, 1,330 and 1,255 cm⁻¹.

NMR signals at $\tau$ = 2.3–2.8 (m, 10H); 4.3 (s), 4.5 (AB J = 4Hz) (a total of 3H); 5.8 (s, 1H); 8.4 + 8.5 ppm (d, 6H).

EXAMPLE 26

If, in the procedure of Example 1B, the Ampicillin used there is replaced by:

D(-)-α-amino-m-methyl-benzylpenicillin,
D(-)-α-amino-p-methyl-benzylpenicillin,
D(-)-α-amino-o-fluoro-benzylpenicillin,
D(-)-α-amino-m-fluoro-benzylpenicillin,
D(-)-α-amino-p-fluoro-benzylpenicillin,
D(-)-α-amino-m-chloro-benzylpenicillin,
D(-)-α-amino-p-chloro-benzylpenicillin,
D(-)-α-amino-p-nitro-benzylpenicillin,
D(-)-α-amino-p-cyano-benzylpenicillin,
D(-)-α-amino-m-methoxy-benzylpenicillin,
D(-)-α-amino-p-methoxy-benzylpenicillin, D(-)-α-amino-m-hydroxy-benzylpenicillin,
D(-)-α-amino-m,p-dihydroxy-benzylpenicillin,
D(-)-α-amino-p-acetoxy-benzylpenicillin,
D(-)-α-amino-p-acetamino-benzylpenicillin,
D(-)-α-amino-p-dimethylamino-benzylpenicillin,
D(-)-α-amino-p-sulphamyl-benzylpenicillin,
D(-)-α-amino-α-2-thienylmethylpenicillin or
D(-)-α-amino-α-3-thienylmethylpenicillin,
the following penicillins are obtained in the form of their sodium salts:

D(-)-α-[(4-methyl-5-oxo-3-pyrazolin-2-yl)-carbonylamino]-m-methyl-benzylpenicillin,
D(-)-α-[(4-methyl-5-oxo-3-pyrazolin-2-yl)-carbonylamino]-p-methyl-benzylpenicillin,
D(-)-α-[(4-methyl-5-oxo-3-pyrazolin-2-yl)-carbonylamino]-o-fluoro-benzylpenicillin,
D(-)-α-[(4-methyl-5-oxo-3-pyrazolin-2-yl)-carbonylamino]-m-fluoro-benzylpenicillin,
D(-)-α-[(4-methyl-5-oxo-3-pyrazolin-2-yl)-carbonylamino]-p-fluoro-benzylpenicillin,
D(-)-α-[(4-methyl-5-oxo-3-pyrazolin-2-yl)-carbonylamino]-m-chloro-benzylpenicillin,
D(-)-α-[(4-methyl-5-oxo-3-pyrazolin-2-yl)-carbonylamino]-p-chloro-benzylpenicillin,
D(-)-α-[(4-methyl-5-oxo-3-pyrazolin-2-yl)-carbonylamino]-p-nitro-benzylpenicillin,
D(-)-α-[(4-methyl-5-oxo-3-pyrazolin-2-yl)-carbonylamino]-p-chloro-benzylpenicillin,
D(-)-α-[(4-methyl-5-oxo-3 pyrazolin-2-yl)-carbonylamino]-p-nitro-benzylpenicillin,
D(-)-α-[(4-methyl-5-oxo-3-pyrazolin-2-yl)-carbonylamino]-p-cyano-benzylpenicillin,
D(-)-α-[(4-methyl-5-oxo-3-pyrazolin-2-yl)-carbonylamino]-m-methoxy-benzylpenicillin,
D(-)-α-[(4-methyl-5-oxo-3-pyrazolin-2-yl)-carbonylamino]-p-methoxy-benzylpenicillin,
D(-)-α-[(4-methyl-5-oxo-3-pyrazolin-2-yl)-carbonylamino]-m-hydroxy-benzylpenicillin,
D(-)-α-[(4-methyl-5-oxo-3-pyrazolin-2-yl)-carbonylamino]-m,p-dihydroxy-benzylpenicillin,
D(-)-α-[(4-methyl-5-oxo-3-pyrazolin-2-yl)-carbonylamino]-p-acetoxy-benzylpenicillin,
D(-)-α-[(4-methyl-5-oxo-3-pyrazolin-2-yl)-carbonylamino]-p-acetamido-benzylpenicillin,
D(-)-α-[(4-methyl-5-oxo-3-pyrazolin-2-yl)-carbonylamino]-p-dimethylamino-benzylpenicillin,
D(-)-α-[(4-methyl-5-oxo-3-pyrazolin-2-yl)-carbonylamino]-p-sulphamyl-benzylpenicillin,
D(-)-α-[(4-methyl-5-oxo-3-pyrazolin-2-yl)-carbonylamino]-α-2-thienyl-methylpenicillin or
D(-)-α-[(4-methyl-5-oxo-3-pyrazolin-2yl)-carbonylamino]-α-3-thienyl-methylpenicillin, respectively.

EXAMPLE 27

If, in the procedure of Example 1B, the Ampicillin used there is replaced by D(-)-α-amino-p-hydroxy-benzylpenicillin or D(-)-α-amino-α-(1,4-cyclohexadien-1-yl)-methylpenicillin, and the 2-chlorocarbonyl-4-methyl-5-oxo-pyrazoline-3 used there is replaced by:

2-chlorocarbonyl-5-oxo-pyrazoline-3,
2-chlorocarbonyl-3-methyl-5-oxo-pyrazoline-3,
2-chlorocarbonyl-4-phenyl-5-oxo-pyrazoline-3,
1-chlorocarbonyl-3-oxo-pyrazolidine,
1-chlorocarbonyl-3-oxo-4-methyl-pyrazolidine,
1-chlorocarbonyl-3-oxo-5-methyl-pyrazolidine,
1-chlorocarbonyl-3-oxo-4-phenyl-pyrazolidine or
1-chlorocarbonyl-3-oxo-5-phenyl-pyrazolidine, the following penicillins are obtained in the form of their sodium salts:

D(-)-α-[(5-oxo-3-pyrazolin-2-yl)-carbonylamino]-p-hydroxy-benzylpenicillin,
D(-)-α-[(3-methyl-5-oxo-3-pyrazolin-2-yl)-carbonylamino]-p-hydroxy-benzylpenicillin,
D(-)-α-[(4-phenyl-5-oxo-3-pyrazolin-2-yl)-carbonylamino]-p-hydroxy-benzylpenicillin,
D(-)-α-[(3-oxo-pyrazolidin-1-yl)-carbonylamino]-p-hydroxy-benzylpenicillin,
D(-)-α-[(3-oxo-4-methyl-pyrazolidin-1-yl)-carbonylamino]-p-hydroxy-benzylpenicillin,
D(-)-α-[(3-oxo-5-methyl-pyrazolidin-1-yl)-carbonylamino]-p-hydroxy-benzylpenicillin,
D(-)-α-[(3-oxo-4-phenyl-pyrazolidin-1-yl)-carbonylamino]-p-hydroxy-benzylpenicillin,
D(-)-α-[(3-oxo-5-phenyl-pyrazolidin-2-yl)-carbonylamino]-p-hydroxy-benzylpenicillin,
D(-)-α-[(5-oxo-3-pyrazolidin-2-yl)-carbonylamino]-α-(1,4-cyclohexadien-1-yl)-methylpenicillin,
D(-)-α-[(3-methyl-5-oxo-pyrazolin-2-yl)-carbonylamino]-α-(1,4-cyclohexadien-1-yl)-methylpenicillin,
D(-)-α-[(4-phenyl-5-oxo-3-pyrazolin-2-yl)-carbonylamino]-α-(1,4-cyclohexadien-1-yl)-methylpenicillin,
D(-)-α-[(3-oxo-pyrazolidin-1-yl)-carbonylamino]-α-1,4-cyclohexadien-1-yl)-methylpenicillin,
D(-)-α-[(3-oxo-4-methyl-pyrazolidin-1-yl)-carbonylamino]-α-(1,4-cyclohexadien-1-yl)-methylpenicillin,
D(-)-α-[(3-oxo-5-methyl-pyrazolidin-1-yl)-carbonylamino]-α-(1,4-cyclohexadien-1-yl)-methylpenicillin,
D(-)-α-[(3-oxo-4-phenyl-pyrazolidin-1-yl)-carbonylamino]-α-(1,4-cyclohexadien-1-yl)-methylpenicillin or
D(-)-α-[(3-oxo-5-phenyl-pyrazolidin-1-yl)-carbonylamino]-α-(1,4-cyclohexadien-1-yl)-methylpenicillin.

EXAMPLE 28

If, in the procedure of Example 1B, the 2-chlorocarbonyl-4-methyl-5-oxo-pyrazoline-3 used there is replaced by:

2-chlorothiocarbonyl-5-oxo-pyrazoline-3,
2-chlorothiocarbonyl-4-methyl-5-oxo-pyrazoline-3,
2-chlorothiocarbonyl-4-phenyl-5-oxo-pyrazoline-3,
2-chlorothiocarbonyl-3-phenyl-5-oxo-pyrazoline-3,
1-chlorothiocarbonyl-3-oxo-pyrazolidine,
1-chlorothiocarbonyl-3-oxo-4-methyl-pyrazolidine,
1-chlorothiocarbonyl-3-oxo-4-phenyl-pyrazolidine,
2-chlorothiocarbonyl-5-oxo-1,2,4-triazoline-3 or
2-chlorothiocarbonyl-3-methyl-5-oxo-1,2,4-triazoline-3 the following penicillins are obtained in the form of their sodium salts:

D(-)-α-[(5-oxo-3-pyrazolin-2-yl)-thiocarbonylamino]-benzylpenicillin,
D(-)-α-[(4-methyl-5-oxo-3-pyrazolin-2-yl)-thiocarbonylamino]-benzylpenicillin,
D(-)-α-[(4-phenyl-5-oxo-3-pyrazolin-2-yl)-thiocarbonylamino]-benzylpenicillin,
D(-)-α-[(3-phenyl-5-oxo-3-pyrazolin-2-yl)-thiocarbonylamino]-benzylpenicillin,
D(-)-α-[(3-oxo-pyrazolidin-1-yl)-thiocarbonylamino]-benzylpenicillin, D(-)-α-[(3-oxo-4-methyl-pyrazolidin-1-yl)-thiocarbonylamino]-benzylpenicillin,
D(-)-α-[(3-oxo-4-phenyl-pyrazolidin-1-yl)-thiocarbonylamino]-benzylpenicillin,
D(-)-α-[(5-oxo-1,2,4-triazol-3-in-2-yl)-thiocarbonylamino]-benzylpenicillin or
D(-)-α-[(3-methyl-5-oxo-1,2,4-triazol-3-in-2-yl)-thiocarbonylamino]-benzylpenicillin, respectively.

EXAMPLE 29

If, in the procedure of Example 1B, the Ampicillin used there is replaced by:
D(-)-α-amino-p-hydroxy-benzylpenicillin,
D(-)-α-amino-α-(1,4-cyclohexadien-1-yl)-methylpenicillin,
D(-)-α-amino-p-chloro-benzylpenicillin or
D(-)-α-amino-p-nitro-benzylpenicillin,
and the 2-chlorocarbonyl-4-methyl-5-oxo-pyrazoline-3 used there is replaced by:
2-chlorothiocarbonyl-5-oxo-pyrazoline-3,
2-chlorothiocarbonyl-4-methyl-5-oxo-pyrazoline-3,
1-chlorothiocarbonyl-3-oxo-pyrazolidine or
1-chlorothiocarbonyl-3-oxo-4-methyl-pyrazolidine,
the following penicillins are obtained in the form of their sodium salts:
D(-)-α-[(5-oxo-3-pyrazolin-2-yl)-thiocarbonylamino]-p-hydroxy-benzylpenicillin,
D(-)-α-[(5-oxo-3-pyrazolin-2-yl)-thiocarbonylamino]-α-(1,4-cyclohexadien-1-yl)-methylpenicillin,
D(-)-α-[(5-oxo-3-pyrazolin-2-yl)-thiocarbonylamino]-p-chloro-benzylpenicillin,
D(-)-α-[(5-oxo-3-pyrazolin-2-yl)-thiocarbonylamino]-p-butriObenzylpenicillin,
D(-)-α-[(4-methyl-5-oxo-3-pyrazolin-2yl)-thiocarbonylamino]-p-hydroxy-benzylpenicillin,
D(-)-α-[(4-methyl-5-oxo-3-pyrazolin-2-yl)-thiocarbonylamino]-α-(1,4-cyclohexadien-1-yl)-methylpenicillin,
D(-)-α-[(4-methyl-5-oxo-3-pyrazolin-2-yl)-thiocarbonylamino]-p-chloro-benzylpenicillin,
D(-)-α-[(4-methyl-5-oxo-3-pyrazolin-2-yl)-thiocarbonylamino]-p-nitro-benzylpenicillin,
D(-)-α-[(3-oxo-pyrazolidin-1-yl)-thiocarbonylamino]-p-hydroxy-benzylpenicillin,
D(-)-α-[(3-oxo-pyrazolidin-1-yl)-thiocarbonylamino]-α-(1,4-cyclohexadien-1-yl)-methylpenicillin,
D(-)-α-[(3-oxo-pyrazolidin-1-yl)-thiocarbonylamino]-p-chloro-benzylpenicillin,
D(-)-α-[(3-oxo-pyrazolidin-1-yl)-thiocarbonylamino]-p-nitro-benzylpenicillin,
D(-)-α-[(3-oxo-4-methyl-pyrazolidin-1-yl)-thiocarbonylamino]-p-hydroxy-benzylpenicillin,
D(-)-α-[(3-oxo-4-methyl-pyrazolidin-1-yl)-thiocarbonylamino]-α-(1,4-cyclohexadien-1-yl)-methylpenicillin,
D(-)-α-[(3-oxo-4-methyl-pyrazolidin-1-yl)-thiocarbonylamino]-p-chloro-benzylpenicillin or
D(-)-α-[(3-oxo-4-methyl-pyrazolidin-1yl)-thiocarbonylamino]-p-nitro-benzylpenicillin.

EXAMPLE 30

(A)

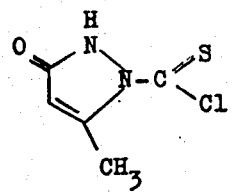

29.4 Parts by weight of 3-methyl-5-oxo-pyrazoline-(2) were dissolved or suspended in 600 parts by volume of tetrahydrofurane and after cooling to 0°–5°C, 23 parts by volume of thiophosgene were added. Triethylamine (42 parts by volume) was then added dropwise with further cooling and the reaction mixture was then left to stand overnight at 0°C. The precipitate present was filtered off and the filtrate was completely evaporated in vacuo. A brown oil was obtained, which solidified after treatment with ether.

Yield: 21.3 parts by weight of 2-chlorothiocarbonyl-3-methyl-5-oxo-pyrazoline-(3).

(B)

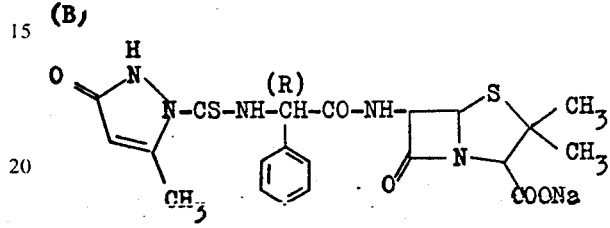

4.0 Parts by weight of Ampicillin were dissolved in 40 parts by volume of 80% strength aqueous tetrahydrofurane at pH 7.0–7.5 by means of triethylamine. 1.9 parts by weight of crude 2-chlorothiocarbonyl-3-methyl-5-oxo-pyrazoline-(3) were added to this solution and the pH was kept constant at 7 by appropriate addition of triethylamine. The mixture was stirred further until it was no longer necessary to add triethylamine to maintain the pH value of 7. It was then diluted with water, the tetrahydrofurane was removed in vacuo, and the residue was covered with ethyl acetate and acidified to pH 1.5. The organic phase was then separated off, washed with water and dried over MgSO$_4$, and the penicillin was precipitated as the sodium salt by means of sodium 2-ethylhexanoate solution.

Yield: 1.4 parts by weight of sodium D(-)-α-[(3-methyl-5-oxo-3-pyrazolin-2-yl)-thiocarbonylamino]-benzylpenicillin.

β-Lactam content: 75%.

The penicillin contained sodium 2ethylhexanoate, ethyl acetate, ether and water, which was taken into account in the calculated analytical data.

Calculated: C 46.3, H 5.7, N 10.8, S 9.9. Found: C 45.4, H 4.8, N 10.5, S 10.2.

EXAMPLE 31

(A)

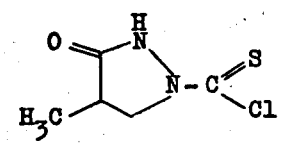

A mixture of 10.8 parts by weight of 4-methyl-5-oxo-pyrazolidine, 100 parts by volume of tetrahydrofurane and 7.7 parts by weight of thiophosgene was stirred overnight at 0°C. The precipitate present was then filtered off and the filtrate was concentrated in vacuo. The precipitate which hereupon separated out was increased in amount by adding ether, filtered off and rapidly recrystallized from nitromethane at 80°C.

Yield: 2.5 parts by weight of 2-chlorothiocarbonyl-4-methyl-5-oxo-pyrazolidine.

Melting point = 156°–160°, with decomposition.
The substance was not entirely pure. It contained 10% of the compound

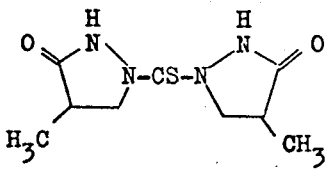

This was taken into account in the calculated analytical data:
Calculated: C 34.9, H 4.1, Cl 17.5, N 16.6, S 17.4.
Found: C 34.2, H 4.3, Cl 17.9, N 17.2, S 17.4.

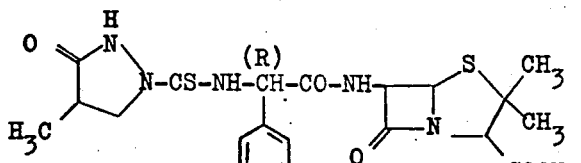

This penicillin was prepared in the manner described in Example 30 from 4.0 parts by weight of Ampicillin and 2.0 parts by weight of 2-chlorothiocarbonyl-4-methyl-5-oxo-pyrazolidine.
Yield: 1.6 parts by weight of sodium D(-)-α-[(4-methyl-5-oxo-pyrazolidin-2-yl)-thiocarbonylamino]-benzylpenicillin.
β-Lactam content: 80%.
Calculated: (H₂O content taken into account): C 43.8, H 5.4, N 12.1, S 11.2. Found: C 44.2, H 5.2, N 11.8, S 11.2.

EXAMPLE 32

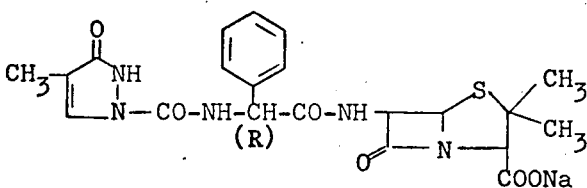

40.3 Parts by weight of Ampicillin in 200 parts by volume of water were adjusted with 2n NaOh to a pH value of 7.5 to 8.0 while stirring and 16.1 parts by weight of 2-chlorocarbonyl-4-methyl-5-oxo-pyrazoline (3) added in portions thereto within 5 minutes, the pH value being maintained at 7.5–8.0 with 2n NaOH. Stirring was continued for about 30 minutes until it was no longer necessary to add NaOH to maintain the pH value. The solution was then extracted with 100 parts by volume of ethyl acetate, which was discarded, 200 parts by volume of ethyl acetate were again added and acidified to a pH value of 2.0 while cooling with ice. The ethyl acetate was separated off, the aqueous phase extracted again and the combined ethyl acetate amounts washed with water and dried over MgSO₄. Thereafter there were added 100 parts by volume of a 1 molar solution of sodium-2-ethylhexanoate in ether containing methanol, the mixture concentrated by evaporation on the rotary evaporator at room temperature until it has reached an oily consistency, dissolved in a little methanol and stirred into 1000 parts by weight of ether/methanol 10:1 (0°C). The mixture is then filtered off by suction, washed with ether and dried over P₂O₅ and paraffin chips.
Yield of sodium D(-)-α-[(4-methyl-5-oxo-pyrazole-3-in-2-yl)-carbonylamino]-benzylpenicillin: 90%.
IR bands at 3,250, 1,760, 1,668, 1,602, 1,503, 1,317 and 1,208 cm⁻¹ in (Nujol).
NMR signals at τ = 2.25 (1H), 2.3–2.8 (5H), 4.3 (1H), 4.5 (2H), 5.8 (1H), 8.05 (3H), 8.4 (3H) and 8.45 ppm (3H) (in CD₃OD).

EXAMPLE 33

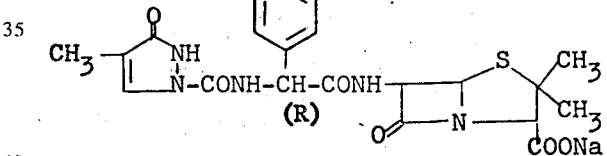

40 parts by weight of Ampicillin-trihydrate in 200 parts by volume of water were adjusted with 2n of sodium hydroxide solution to a pH value of 8.0 and 16.1 parts by weight of 2-chlorocarbonyl-4-methyl-5-oxo-pyrazoline (3) added in portions thereto in the course of 15 minutes, the pH being maintained at 8 by the sodium hydroxide solution. Stirring was continued until it was no longer necessary to add sodium hydroxide solution to maintain a pH value of 8 (approx. 30 minutes). The solution was then extracted with 100 parts by volume of ether, which was discarded, and covered with 150 parts by volume of fresh ether. A pH value of 2 was then adjusted with 2n HCl while cooling with ice and stirring, the ether separated off, the aqueous phase again extracted with 110 parts by volume of ether and the combined ether solutions extracted by shaking with 50 parts by volume of water. 10 g of MgSO₄ were thoroughly mixed with the ether for 5 minutes, decanted and the ether again stirred with 20 g of MgSO₄ for 1 hour. The mixture was then filtered off by suction without washing again.
In the meantime 3.8 parts by weight of sodium were dissolved in 260 parts by volume of anhydrous ethanol, 13.7 parts by weight of 2-ethyl-caproic acid and 12 parts by volume of water added and cooled to 0°C. The above prepared ether solution is added while stirring to the penicillin acid, inoculated and stirred for 24 hours at room temperature. The penicillin sodium salt which has crystallized out was filtered off by suction, suspended with 50 parts by volume of ether/ethanol 3:2, filtered again and washed with 100 parts by volume of ether.

Yield of crystallized sodium D(-)-α-[(4-methyl-5-oxo-pyrazole-3-in-2-yl)-carbonylamino]-benzylpenicillin: 28.3 parts by weight = 57%.

IR bands at 3,320, 1,784, 1,716, 1,674, 1,615, 1,596, 1,300 and 1,195 cm$^{-1}$ (in Nujol).

What is claimed is:

1. A pharmaceutical composition for treating bacterial infections in humans and animals which comprises an antibacterially effective amount of a compound of the formula:

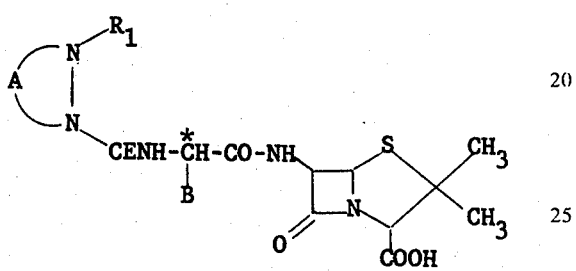

or a pharmaceutically acceptable nontoxic salt thereof wherein $R_1$ is hydrogen, straight or branched chain alkyl of 1 to 5 carbon atoms, monoaralkyl of up to 8 carbon atoms, monoaryl, or thienyl;

A is

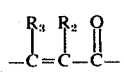

wherein $R_2$ and $R_3$ are the same or different and each is hydrogen, straight or branched chain alkyl of 1 to 5 carbon atoms, monoaralkyl of up to 8 carbon atoms, monoaryl, or thienyl;

R is:

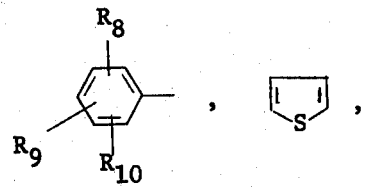

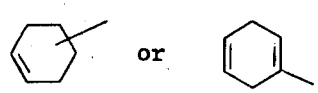

wherein $R_8$, $R_9$ and $R_{10}$ are the same or different and each is hydrogen, fluoro, chloro, bromo, iodo, lower alkyl, lower alkoxy, lower alkylthio, lower alkylsulphonyl, sulphamyl, nitro, cyano, di(lower alkyl) amino, lower alkanoylamino, lower alkanoyloxy, lower alkylsulphonylamino, trifluoromethyl or hydroxy;

E is oxygen or sulphur; and

*C is a carbon atom constituting a center of chirality in combination with a pharmaceutical carrier.

2. A composition according to claim 1 wherein $R_1$ is hydrogen, or straight or branched chain alkyl of 1 to 4 carbon atoms;

$R_2$ and $R_3$ are the same or different and each is hydrogen, alkyl of 1 to 4 carbon atoms, phenyl or hydroxyphenyl;

B is:

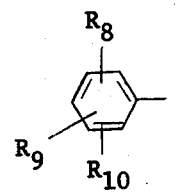

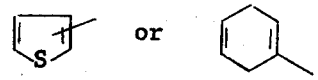

wherein $R_8$, $R_9$ and $R_{10}$ are the same or different and each is hydrogen, fluoro, chloro, bromo, iodo, lower alkyl, lower alkoxy, lower alkylthio, lower alkylsulphonyl, sulphamyl, nitro, cyano, diamino, lower alkanoylamino, lower alkanoyloxy, lower alkylsulphonylamino, trifluoromethyl or hydroxy.

3. A composition according to claim 2 wherein *C is in the R— configuration.

4. A composition according to claim 1 wherein $R_1$ is hydrogen;

$R_2$ and $R_3$ are the same or different and each is hydrogen or methyl; and

B is phenyl, hydroxyphenyl, thienyl or cyclohexadien-1-yl.

5. A composition according to claim 4 wherein *C is in the R— configuration.

6. A composition according to claim 1 wherein $R_1$ is hydrogen or lower alkyl;

$R_2$ and $R_3$ are both hydrogen, one is alkyl of 1 to 4 carbon atoms, phenyl or nitrophenyl and the other is hydrogen, or both are methyl;

B is phenyl, hydroxyphenyl or cyclohexadien-1-yl; and

*C is in the R— configuration.

7. A composition according to claim 1 wherein $R_1$ is hydrogen or methyl;

$R_2$ and $R_3$ are each hydrogen, one is methyl, ethyl, phenyl or nitrophenyl and the other is hydrogen, or both are methyl;

B is phenyl, p-hydroxyphenyl or cyclohexadien-1-yl; and

*C is in the R-configuration.

8. A composition according to claim 1 wherein $R_1$ is hydrogen, methyl or ethyl;

$R_2$ and $R_3$ are each hydrogen, one is alkyl of 1 to 4 carbon atoms, phenyl or nitrophenyl and the other is hydrogen, or both are methyl;

B is phenyl; phenyl substituted by fluoro, chloro, bromo, lower alkyl, lower alkoxy, nitro, cyano, diamino, lower alkanoylamino, lower alkanoyloxy, sulphamyl, hydroxy or dihydroxy; cyclohexadien-1-yl; or thienyl; and $\overset{*}{C}$ is is the R- configuration.

9. A composition according to claim 1 wherein
$R_1$ is hydrogen or methyl;

$R_2$ and $R_3$ are each hydrogen, one is methyl, ethyl, phenyl or nitrophenyl and the other is hydrogen, or both are methyl;

B is phenyl; phenyl substituted by hydroxy, methyl, fluoro, chloro, nitro, cyano, methoxy, acetoxy, acetamido, dimethylamino, sulphamyl, or$_*$ dihydroxy; cyclohexadien-1-yl; or thienyl; and $\overset{*}{C}$ is in the R— configuration.

10. A composition according to claim 1 wherein the compound is in the form of a salt selected from the group consisting of the sodium, potassium, magnesium, calcium, aluminum, ammonium, a diamine, a triamine, procaine, dibenzylamine, N,N′-dibenzylethylenediamine, N-benzyl-β-phenethylamine, N-methylmorpholine, N-ethylmorpholine, 1-ephenamine, dehydrobietylamine, N,N′-bis-dehydroabietylethylenediamine, and N-lower alkylpiperidine salts.

11. A composition according to claim 1 wherein the compound is in the form of the sodium salt and $\overset{*}{C}$ is in the R— configuration.

12. A composition according to claim 1 wherein the compound is D(-)-α-[(4-methyl-5-oxo-3-pyrazolin-2-yl)-carbonylamino]-benzylpenicillin or the sodium salt thereof.

13. A composition according to claim 1 wherein the compound is D(-)-α-[(4-phenyl-5-oxo-3-pyrazolin-2-yl)-carbonylamino]-benzylpenicillin of the sodium salt thereof.

14. A composition according to claim 1 wherein the compound is D(-)-α-[(3-methyl-5-oxo-3-pyrazolin-2-yl)-carbonylamino]-benzylpenicillin or the sodium salt thereof.

15. A composition according to claim 1 wherein the compound is D(-)-α-[(3-phenyl-5-oxo-pyrazolin-(3)-2-yl)-carbonylamino]-benzylpenicillin or the sodium salt thereof.

16. A composition according to claim 1 wherein the compound is D(-)-α-[(3-p-nitrophenyl-5-oxo-pyrazolin-(3)-2-yl)-carbonylamino]-benzylpenicillin or the sodium salt thereof.

17. A composition according to claim 1 wherein the compound is D(-)-α-[(3-m-nitrophenyl-5-oxo-pyrazolin-(3)-2-yl)-carbonylamino]-benzylpenicillin or the sodium salt thereof.

18. A composition according to claim 1 wherein the compound is D(-)-α-[(2-methyl-4-phenyl-5-oxo-3-pyrazolin-1-yl)-carbonylamino]-benzylpenicillin or the sodium salt thereof.

19. A composition according to claim 1 wherein the compound is D(-)-α-[(4-methyl-5-oxo-3-pyrazolin-2-yl)-carbonylamino]-p-hydroxybenzylpenicillin or the sodium salt thereof.

20. A composition according to claim 1 wherein the compound is D(-)-α-[4-methyl-5-oxo-3-pyrazolin-2-yl)-carbonylamino]-α-(cyclohexa-1,4-dien-1-yl)-methylpenicillin or the sodium salt thereof.

21. A composition according to claim 1 wherein the compound is D(-)-α-[(4-methyl-5-oxo-3-pyrazolin-2-yl)-carbonylamino]-m-methyl-benzylpenicillin or the sodium salt thereof.

22. A composition according to claim 1 wherein the compound is D(-)-α-[(4-methyl-5-oxo-3-pyrazolin-2-yl)-carbonylamino]-p-methyl-benzylpenicillin or the sodium salt thereof.

23. A composition according to claim 1 wherein the compound is D(-)-α-[(4-methyl-5-oxo-3-pyrazolin-2-yl)-carbonylamino]-o-fluoro-benzylpenicillin or the sodium salt thereof.

24. A composition according to claim 1 wherein the compound is D(-)-α[(4-methyl-5-oxo-3-pyrazolin-2-yl)-carbonylamino]-m-fluoro-benzylpenicillin or the sodium salt thereof.

25. A composition according to claim 1 wherein the compound is D(-)-α-[(4-methyl-5-oxo-3-pyrazolin-2-yl)-carbonylamino]-p-fluoro-benzylpenicillin or the sodium salt thereof.

26. A composition according to claim 1 wherein the compound is D(-)-α-[(4-methyl-5-oxo-3-pyrazolin-2-yl)-carbonylamino]-m-chloro-benzylpenicillin or the sodium salt thereof.

27. A compound according to claim 1 wherein the compound is D(-)-α-[(4-methyl-5-oxo-3-pyrazolin-2-yl)-carbonylamino]-p-chloro-benzylpenicillin or the sodium salt thereof.

28. A composition according to claim 1 wherein the compound is D(-)-α-[(4-methyl-5-oxo-3-pyrazolin-2-yl)-carbonylamino]-p-nitro-benzylpenicillin or the sodium salt thereof.

29. A composition according to claim 1 wherein the compound is D(-)-α-[(4-methyl-5-oxo-3-pyrazolin-2-yl)-carbonylamino]-p-cyano-benzylpenicillin or the sodium salt thereof.

30. A composition according to claim 1 wherein the compound is D(-)-α-[(4-methyl-5-oxo-3-pyrazolin-2-yl)-carbonylamino]-m-methoxybenzylpenicillin or the sodium salt thereof.

31. A composition according to claim 1 wherein the compound is D(-)-α-[(4-methyl-5-oxo-3-pyrazolin-2-yl)-carbonylamino]-p-methoxybenzylpenicillin or the sodium salt thereof.

32. A composition according to claim 1 wherein the compound is D(-)-α-[(4-methyl-5-oxo-3-pyrazolin-2-yl)-carbonylamino]-m-hydroxybenzylpenicillin or the sodium salt thereof.

33. A composition according to claim 1 wherein the compound is D(-)-α-[(4-methyl-5-oxo-3-pyrazolin-2-yl)-carbonylamino]-m,p-dihydroxybenzylpenicillin or the sodium salt thereof.

34. A composition according to claim 1 wherein the compound is D(-)-α-[(4-methyl-5-oxo-3-pyrazolin-2-yl)-carbonylamino]-p-acetoxybenzylpenicillin or the sodium salt thereof.

35. A composition according to claim 1 wherein the compound is D(-)-α-[(4-methyl-5-oxo-3-pyrazolin-2-yl)-carbonylamino]-p-acetamidobenzylpenicillin or the sodium salt thereof.

36. A composition according to claim 1 wherein the compound is D(-)-α-[(4-methyl-5-oxo-3-pyrazolin-2-yl)-carbonylamino]-p-dimethylaminobenzylpenicillin or the sodium salt thereof.

37. A composition according to claim 1 wherein the compound is D(-)-α-[(4-methyl-5-oxo-3-pyrazolin-2-yl)-carbonylamino]-p-sulphamylbenzylpenicillin or the sodium salt thereof.

38. A composition according to claim 1 wherein the compound is D(-)-α-[(4-methyl-5-oxo-3-pyrazolin-2-yl)-carbonylamino]-α-2-thienylmethylpenicillin or the sodium salt thereof.

39. A composition according to claim 1 wherein the compound is D(-)-α-[(4-methyl-5-oxo-3-pyrazolin-2-yl)-carbonylamino]-α-3-thienylmethylpenicillin or the sodium salt thereof.

40. A composition according to claim 1 wherein the compound is D(-)-α-[(5-oxo-3-pyrazolin-2-yl)-carbonylamino]-p-hydroxybenzylpenicillin or the sodium salt thereof.

41. A composition according to claim 1 wherein the compound is D(-)-α-[(3-methyl-5-oxo-3-pyrazolin-2-yl)-carbonylamino]-p-hydroxybenzylpenicillin or the sodium salt thereof.

42. A composition according to claim 1 wherein the compound is D(-)-α-[(4-phenyl-5-oxo-3-pyrazolin-2-yl)-carbonylamino]-p-hydroxybenzylpenicillin or the sodium salt thereof.

43. A composition according to claim 1 wherein the compound is D(-)-α-[(3-methyl-5-oxo-pyrazolin-2-yl)-carbonylamino]α-(1,4-cyclohexadien-1-yl)-methyl-penicillin or the sodium salt thereof.

44. A composition according to claim 1 wherein the compound is D(-)-α-[(4-phenyl-5-oxo-3-pyrazolin-2-yl)-carbonylamino]-α-(1,4-cyclohexadien-1-yl)-methylpenicillin or the sodium salt thereof.

45. A composition according to claim 1 wherein the compound is D(-)-α-[(5-oxo-3-pyrazolin-2-yl)-thiocarbonylamino]-benzylpenicillin or the sodium salt thereof.

46. A composition according to claim 1 wherein the compound is D(-)-α-[(4-methyl-5-oxo-3-pyrazolin-2-yl)-thiocarbonylamino]-benzylpenicillin or the sodium salt thereof.

47. A composition according to claim 1 wherein the compound is D(-)-α-[(4-phenyl-5-oxo-3-pyrazolin-2-yl)-thiocarbonylamino]-benzylpenicillin or the sodium salt thereof.

48. A composition according to claim 1 wherein the compound is D(-)-α-[(3-phenyl-5-oxo-3-pyrazolin-2-yl)-thiocarbonylamino]-benzylpenicillin or the sodium salt thereof.

49. A composition according to claim 1 wherein the compound is D(-)-α-[(5-oxo-3-pyrazolin-2-yl)-thiocarbonylamino]-p-hydroxy-benzylpenicillin or the sodium salt thereof.

50. A composition according to claim 1 wherein the compound is D(-)-α-[(5-oxo-3-pyrazolin-2-yl)-thiocarbonylamino]-α-(1,4-cyclohexadien-1-yl)-methylpenicillin or the sodium salt thereof.

51. A composition according to claim 1 wherein the compound is D(-)-α-[(5-oxo-3-pyrazolin-2-yl)-thiocarbonylamino]-p-chloro-benzylpenicillin or the sodium salt thereof.

52. A composition according to claim 1 wherein the compound is D(-)-α-[(5-oxo-3-pyrazolin-2-yl)-thiocarbonylamino]-p-nitro-benzylpenicillin or the sodium salt thereof.

53. A composition according to claim 1 wherein the compound is D(-)-α-[(4-methyl-5-oxo-3-pyrazolin-2-yl)-thiocarbonylamino]-p-hydroxybenzylpenicillin or the sodium salt thereof.

54. A composition according to claim 1 wherein the compound is D(-)-α-[(4-methyl-5-oxo-3-pyrazolin-2-yl)-thiocarbonylamino]-α-(1,4-cyclohexadien-1-yl)-methylpenicillin or the sodium salt thereof.

55. A composition according to claim 1 wherein the compound is D(-)-α-[(4-methyl-5-oxo-3-pyrazolin-2-yl)-thiocarbonylamino]-p-chlorobenzylpenicillin or the sodium salt thereof.

56. A composition according to claim 1 wherein the compound is D(-)-α-[(4-methyl-5-oxo-3-pyrazolin-2-yl)-thiocarbonylamino]-p-nitrobenzylpenicillin or the sodium salt thereof.

57. A composition according to claim 1 wherein the compound is D(-)-α-[(4-methyl-5-oxo-3-pyrazolin-2-yl)-thiocarbonylamino]-p-nitrobenzylpenicillin or the sodium salt thereof.

58. A composition according to claim 1 wherein the compound is D(-)-α-[(5-oxo-3-pyrazolin-2-yl)-carbonylamino]-benzylpenicillin or the sodium salt thereof.

59. A composition according to claim 1 wherein the compound is D(-)-α-[(5-oxo-3-pyrazolin-2-yl)-carbonylamino]-α-(cyclohexa-1,4-dien-1-yl)-methylpenicillin or the sodium salt thereof.

60. A composition according to claim 1 in oral administration form.

61. A composition according to claim 1 in parenteral administration form.

62. A composition according to claim 1 in topical application form.

63. An animal feedstuff which comprises a nutritious material in combination with an antibacterially effective amount of a compound of calim 1.

64. A composition useful for promoting growth in animals which comprises a growth promoting amount of a compound of claim 1 in combination with an animal fodder or animal drinking water.

65. A method of enhancing the growth of animals which comprises feeding to such animal a growth promoting amount of a compound of claim 1.

66. A method of treating bacterial infections in humans and animals which comprises administering to said human or animal an antibacterially effective amount of a compound of the formula:

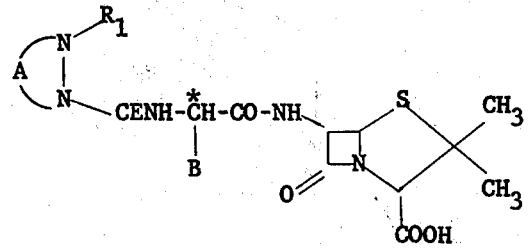

or a pharmaceutically acceptable nontoxic salt thereof wherein $R_1$ is hydrogen, straight or branched chain alkyl of 1 to 5 carbon atoms, monoaralkyl of up to 8 carbon atoms, monoaryl, or thienyl;

A is

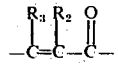

wherein $R_2$ and $R_3$ are the same or different and each is hydrogen, straight or branched chain alkyl of 1 to 5 carbon atoms, monoaralkyl of up to 8 carbon atoms, monoaryl, or thienyl;

B is;

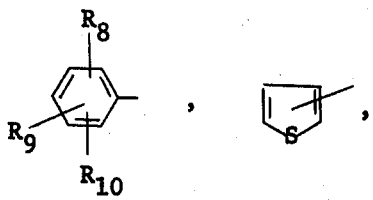

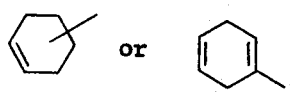

wherein
R$_8$, R$_9$ and R$_{10}$ are the same or different and each is hydrogen, fluoro, chloro, bromo, iodo, lower alkyl, lower alkoxy, lower alkylthio, lower alkylsulphonyl, sulphamyl, nitro, cyano, di(lower alkyl)amino, lower alkanoylamino, lower alkanoyloxy, lower alkylsulphonylamino, trifluoromethyl or hydroxy;
E is oxygen or sulphur; and
$\overset{*}{C}$ is a carbbon atom constituting a center of chirality.

67. A method according to claim 66 wherein
R$_1$ is hydrogen, or straight or branched chain alkyl of 1 to 4 carbon atoms;
R$_2$ and R$_3$ are the same or different and each is hydrogen, alkyl of 1 to 4 carbon atoms, phenyl or hydroxyphenyl;
B is:

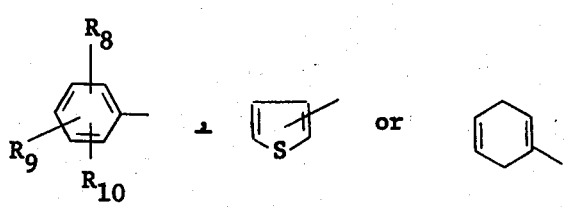 

wherein
R$_8$, R$_9$ and R$_{10}$ are the same or different and each is hydrogen, fluoro, chloro, bromo, iodo, lower alkyl, lower alkoxy, lower alkylthio, lower alkylsulphonyl, sulphamyl, nitro, cyano, di(lower alkyl)amino, lower alkanoylamino, lower alkanoyloxy, lower alkylsulphonylamino, trifluoromethyl or hydroxy.

68. A method according to claim 67 wherein $\overset{*}{C}$ is in the R- configuration.

69. A method according to claim 66 wherein R$_1$ is hydrogen;

R$_2$ and R$_3$ are the same or different and each is hydrogen or methyl;
B is phenyl, hydroxyphenyl, thienyl or cyclohexa-1,4-dien-1-yl.

70. A method according to claim 69 wherein $\overset{*}{C}$ is in the R— configuration.

71. A method according to calim 66 wherein
R$_1$ is hydrogen or lower alkyl;
R$_2$ and R$_3$ are each hydrogen, one is alkyl of 1 to 4 carbon atoms, phenyl or nitrophenyl and the other is hydrogen, or both are methyl;
B is phenyl, hydroxyphenyl or cyclohexadien-1-yl; and
$\overset{*}{C}$ is in the R— configuration.

72. A method according to claim 66 wherein
R$_1$ is hydrogen or methyl;
R$_2$ and R$_3$ are each hydrogen, one is methyl, ethyl, phenyl or nitrophenyl and the other is hydrogen, or both are methyl;
B is phenyl, p-hydroxyphenyl or cyclohexadien-1-yl; and
C is the R— configuration.

73. A method according to claim 66 wherein
R$_1$ is hydrogen, or alkyl of 1 or 2 carbon atoms;
R$_2$ and R$_3$ are each hydrogen, one is alkyl of 1 to 4 carbon atoms, phenyl or nitrophenyl and the other is hydrogen, or both are methyl;
B is phenyl; phenyl substituted by fluoro, chloro, bromo, lower alkyl, lower alkoxy, nitro, cyano, di(lower alkyl)amino, lower alkanoylamino, lower alkanoyloxy, sulphamyl, hydroxy or dihydroxy; cyclohexadien-1-yl; or thienyl; and
$\overset{*}{C}$ is in the R— configuration.

74. A method according to claim 66 wherein
R$_1$ is hydrogen or methyl;
R$_2$ and R$_3$ are each hydrogen, one is methyl, ethyl, phenyl or nitrophenyl and the other is hydrogen, or both are methyl;
B is phenyl; phenyl substituted by hydroxy, methyl, fluoro, chloro, nitro, cyano, methoxy, acetoxy, acetamido, dimethylamino, sulphamyl, or dihydroxy; cyclohexadien-1-yl; or thienyl; and
$\overset{*}{C}$ is in the R— configuration.

75. A method according to claim 66 wherein the compound is in the form of a salt selected from the group consisting of the sodium, potassium, magnesium, calcium, aluminum, ammonium, a di(lower alkyl)amine, a tri(lower alkyl)amine, procaine, dibenzylamine, N,N'-dibenzylethylenediamine, N-benzyl-$\beta$-phenethylamine, N-methylmorpholine, N-ethylmorpholine, 1-ephenamine, dehydroabietylamine, N,N'-bis-dehydroabietylethylenediamine, and N-lower alkylpiperidine salts.

76. A method according to claim 66 wherein the compound is in the form of the sodium salt wherein $\overset{*}{C}$ is in the R— configuration.

77. A method according to claim 66 wherein the compound is D(-)-α-[(4-methyl-5-oxo-3-pyrazolin-2-yl)-carbonylamino]-benzylpenicillin or the sodium salt thereof.

78. A method according to claim 66 wherein the compound is D(-)-α-[(4-phenyl-5-oxo-3-pyrazolin-2-yl)-carbonylamino]-benzylpenicillin or the sodium salt thereof.

79. A method according to claim 66 wherein the compound is D(-)-α-[(3-methyl-5-oxo-3-pyrazolin-2-yl)-carbonylamino]-benzylpenicillin or the sodium salt thereof.

80. A method according to claim 66 wherein the compound is D(-)-α-[(3-phenyl-5-oxo-pyrazolin-(3)-2-yl)-carbonylamino]-benzylpenicillin or the sodium salt thereof.

81. A method according to claim 66 wherein the compound is D(-)-α-[(3-p-nitrophenyl-5-oxo-pyrazolin(3)-2-yl)-carbonylamino]-benzylpenicillin or the sodium salt thereof.

82. A method according to claim 66 wherein the compound is D(-)-α-[(3-m-nitrophenyl-5-oxo-pyrazolin-(3)-2-yl)-carbonylamino]-benzylpenicillin or the sodium salt thereof.

83. A method according to claim 66 wherein the compound is D(-)-α-[(2-methyl-4-phenyl-5-oxo-3-pyrazolin-1-yl)-carbonylamino]-benzylpenicillin or the sodium salt thereof.

84. A method according to claim 66 wherein the compound is D(-)-α-[(4-methyl-5-oxo-3-pyrazolin-2-yl)-carbonylamino]-p-hydroxybenzylpenicillin or the sodium salt thereof.

85. A method according to claim 66 wherein the compound is D(-)-α-[(4-methyl-5-oxo-3-pyrazolin-2-yl)-carbonylamino]-α-(cyclohexa-1,4-dien-1-yl)-methylpenicillin or the sodium salt thereof.

86. A method according to claim 66 wherein the compound is D(-)-α-[(4-methyl-5-oxo-3-pyrazolin-2-yl)-carbonylamino]-m-methylbenzylpenicillin or the sodium salt thereof.

87. A method according to claim 66 wherein the compound is D(-)-α-[(4-methyl-5-oxo-3-pyrazolin-2-yl)-carbonylamino]-p-methylbenzylpenicillin or the sodium salt thereof.

88. A method according to claim 66 wherein the compound is D(-)-α-[(4-methyl-5-oxo-3-pyrazolin-2-yl)-carbonylamino]-o-fluorobenzylpenicillin or the sodium salt thereof.

89. A method according to claim 66 wherein the compound is D(-)-α-[(4-methyl-5-oxo-3-pyrazolin-2-yl)-carbonylamino]-m-fluorobenzylpenicillin or the sodium salt thereof.

90. A method according to claim 66 wherein the compound is D(-)-α-[(4-methyl-5-oxo-3-pyrazolin-2-yl)-carbonylamino]-p-fluorobenzylpenicillin or the sodium salt thereof.

91. A method according to claim 66 wherein the compound is D(-)-α-[(4-methyl-5-oxo-3-pyrazolin-2-yl)-carbonylamino]-m-chlorobenzylpenicillin or the sodium salt thereof.

92. A method according to claim 66 wherein the compound is D(-)-α-[(4-methyl-5-oxo-3-pyrazolin-2-yl)-carbonylamino]-p-chlorobenzylpenicillin or the sodium salt thereof.

93. A method according to claim 66 wherein the compound is D(-)-α-[(4-methyl-5-oxo-3-pyrazolin-2-yl)-carbonylamino]-p-nitrobenzylpenicillin or the sodium salt thereof.

94. A method according to claim 66 wherein the compound is D(-)-α-[(4-methyl-5-oxo-3-pyrazolin-2-yl)-carbonylamino]-p-cyanobenzylpenicillin or the sodium salt thereof.

95. A method according to claim 66 wherein the compound is D(-)-α-[(4-methyl-5-oxo-3-pyrazolin-2-yl)-carbonylamino]-m-methoxybenzylpenicillin or the sodium salt thereof.

96. A method according to claim 66 wherein the compound is D(-)-α-[(4-methyl-5-oxo-3-pyrazolin-2-yl)-carbonylamino]-p-methoxybenzylpenicillin or the sodium salt thereof.

97. A method according to claim 66 wherein the compound is D(-)-α-[(4-methyl-5-oxo-3-pyrazolin-2-yl)-carbonylamino]-m-hydroxybenzylpenicillin or the sodium salt thereof.

98. A method according to claim 66 wherein the compound is D(-)-α-[(4-methyl-5-oxo-3-pyrazolin-2-yl)-carbonylamino]-m,p-dihydroxybenzylpenicillin or the sodium salt thereof.

99. A method according to claim 66 wherein the compound is D(-)-α-[(4-methyl-5-oxo-3-pyrazolin-2-yl)-carbonylamino]-p-acetoxybenzylpenicillin or the sodium salt thereof.

100. A method according to claim 66 wherein the compound is D(-)-α-[(4-methyl-5-oxo-3-pyrazolin-2-yl)-carbonylamino]-p-acetamidobenzylpenicillin or the sodium salt thereof.

101. A method according to claim 66 wherein the compound is D(-)-α-[(4-methyl-5-oxo-3-pyrazolin-2-yl)-carbonylamino]-p-dimethylaminobenzylpenicillin or the sodium salt thereof.

102. A method according to claim 66 wherein the compound is D(-)-α-[(4-methyl-5-oxo-3-pyrazolin-2-yl)-carbonylamino]-p-sulphamylbenzylpenicillin or the sodium salt thereof.

103. A method according to claim 66 wherein the compound is D(-)-α-[(4-methyl-5-oxo-3-pyrazolin-2-yl)-carbonylamino]-α-2-thienylmethylpenicillin or the sodium salt thereof.

104. A method according to claim 66 wherein the compound is D(-)-α-[(4-methyl-5-oxo-3-pyrazolin-2-yl)-carbonylamino]-α-3-thienylmethylpenicillin or the sodium salt thereof.

105. A method according to claim 66 wherein the compound is D(-)-α-[(5-oxo-3-pyrazolin-2-yl)-carbonylamino]-p-hydroxybenzylpenicillin or the sodium salt thereof.

106. A method according to claim 66 wherein the compound is D(-)-α-[(3-methyl-5-oxo-3-pyrazolin-2-yl)-carbonylamino]-p-hydroxybenzylpenicillin or the sodium salt thereof.

107. A method according to claim 66 wherein the compound is D(-)-α-[(4-phenyl-5-oxo-3-pyrazolin-2-yl)-carbonylamino]-p-hydroxybenzylpenicillin or the sodium salt thereof.

108. A method according to claim 66 wherein the compound is D(-)-α-[(3-methyl-5-oxo-pyrazolin-2-yl)-carbonylamino]-α-(1,4-cyclohexadien-1-yl)-methylpenicillin or the sodium salt thereof.

109. A method according to claim 66 wherein the compound is D(-)-α-[(4-phenyl-5-oxo-3-pyrazolin-2-yl)-carbonylamino]-α-(1,4-cyclohexadien-1-yl)-methylpenicillin or the sodium salt thereof.

110. A method according to claim 66 wherein the compound is D(-)-α-[(5-oxo-3-pyrazolin-2-yl)-thiocarbonylamino]-benzylpenicillin or the sodium salt thereof.

111. A method according to claim 66 wherein the compound is D(-)-α-[(4-methyl-5-oxo-3-pyrazolin-2-yl)-thiocarbonylamino]-benzylpenicillin or the sodium salt thereof.

112. A method according to claim 66 wherein the compound is D(-)-α-[(4-phenyl-5-oxo-3-pyrazolin-2-yl)-thiocarbonylamino]-benzylpenicillin or the sodium salt thereof.

113. A method according to claim 66 wherein the compound is D(-)-α-[(3-phenyl-5-oxo-3-pyrazolin-2-yl)-thiocarbonylamino]-benzylpenicillin or the sodium salt thereof.

114. A method according to claim 66 wherein the compound is D(-)-α-[(5-oxo-3-pyrazolin-2-yl)-thiocarbonylamino]-p-hydroxybenzylpenicillin or the sodium salt thereof.

115. A method according to claim 66 wherein the compound is D(-)-α-[(5-oxo-3-pyrazolin-2-yl)-thiocarbonylamino]-α-(1,4-cyclohexadien-1-yl)-methylpenicillin or the sodium salt thereof.

116. A method according to claim 66 wherein the compound is D(-)-α-[(5-oxo-3-pyrazolin-2-yl)-thiocarbonylamino]-p-chlorobenzylpenicillin or the sodium salt thereof.

117. A method according to claim 66 wherein the compound is D(-)-α-[(5-oxo-3-pyrazolin-2-yl)-thiocarbonylamino]-p-nitrobenzylpenicillin or the sodium salt thereof.

118. A method according to claim 66 wherein the compound is D(-)-α-[(4-methyl-5-oxo-3-pyrazolin-2-yl)-thiocarbonylamino]-p-hydroxybenzylpenicillin or the sodium salt thereof.

119. A method according to claim 66 wherein the compound is D(-)-α-[(4-methyl-5-oxo-3-pyrazolin-2-yl)-thiocarbonylamino]-α-(1,4-cyclohexadien-1-yl)-methylpenicillin or the sodium salt thereof.

120. A method according to claim 66 wherein the compound is D(-)-α-[(4-methyl-5-oxo-3-pyrazolin-2-yl)-thiocarbonylamino]-p-chlorobenzylpenicillin or the sodium salt thereof.

121. A method according to claim 66 wherein the compound is D(-)-α-[(4-methyl-5-oxo-3-pyrazolin-2-yl)-thiocarbonylamino]-p-nitrobenzylpenicillin or the sodium salt thereof.

122. A method according to claim 66 wherein the compound is D(-)-α-[(3-methyl-5-oxo-3-pyrazolin-2-yl)-thiocarbonylamino]-benzylpenicillin or the sodium salt thereof.

123. A method according to claim 66 wherein the compound is D(-)-α-[(5-oxo-3-pyrazolin-2-yl)-carbonylamino]-benzylpenicillin or the sodium salt thereof.

124. A method according to claim 66 wherein the compound is D(-)-α-[(5-oxo-3-pyrazolin-2-yl)-carbonylamino]-α-(cyclohexa-1,4-dien-1-yl)-methylpenicillin or the sodium salt thereof.

125. A method according to claim 66 wherein the administration is oral.

126. A method according to claim 66 wherein the administration is parenteral.

127. A method according to claim 66 wherein the administration is by topical application.

* * * * *